(12) United States Patent
Olde et al.

(10) Patent No.: US 9,636,447 B2
(45) Date of Patent: May 2, 2017

(54) FILTERING OF A TIME-DEPENDENT PRESSURE SIGNAL

(75) Inventors: Bo Olde, Lund (SE); Kristian Solem, Kavlinge (NO); Mattias Holmer, Lund (SE); Jan Sternby, Lund (SE)

(73) Assignee: Gambro Lundia AB, Lund (SE)

( * ) Notice: Subject to any disclaimer, the term of this patent is extended or adjusted under 35 U.S.C. 154(b) by 699 days.

(21) Appl. No.: 14/234,527

(22) PCT Filed: Jun. 20, 2012

(86) PCT No.: PCT/EP2012/061765
§ 371 (c)(1),
(2), (4) Date: May 5, 2014

(87) PCT Pub. No.: WO2013/000777
PCT Pub. Date: Jan. 3, 2013

(65) Prior Publication Data
US 2014/0231319 A1   Aug. 21, 2014

Related U.S. Application Data

(60) Provisional application No. 61/502,878, filed on Jun. 30, 2011.

(30) Foreign Application Priority Data

Jun. 30, 2011   (SE) ..................... 1150604

(51) Int. Cl.
*A61B 5/02*   (2006.01)
*A61M 1/36*   (2006.01)
(Continued)

(52) U.S. Cl.
CPC ....... *A61M 1/3607* (2014.02); *A61B 5/02108* (2013.01); *A61B 5/6866* (2013.01);
(Continued)

(58) Field of Classification Search
CPC . A61B 5/021; A61B 5/02108; A61B 5/02116; A61B 5/02125; A61B 5/6866;
(Continued)

(56) References Cited

U.S. PATENT DOCUMENTS 4,642,800 A   2/1987   Umeda
4,667,680 A   5/1987   Ellis
(Continued)

FOREIGN PATENT DOCUMENTS

WO   97/10013   3/1997
WO   00/72750   12/2000
(Continued)

OTHER PUBLICATIONS

Prosecution history of U.S. Appl. No. 13/001,314 (now issued U.S. Pat. No. 9,442,036) filed Dec. 23, 2010.
(Continued)

*Primary Examiner* — Joseph Drodge
(74) *Attorney, Agent, or Firm* — K&L Gates LLP

(57) ABSTRACT

A device removes first pulses in a pressure signal of a pressure sensor which is arranged in a fluid containing system to detect the first pulses, which originate from a first pulse generator, and second pulses, which originate from a second pulse generator. The first pulse generator operates in a sequence of pulse cycles, each pulse cycle resulting in at least one first pulse. The device repetitively obtains a current data sample, calculates a corresponding reference value and subtracts the reference value from the current data sample. The reference value is calculated as a function of other data sample(s) in the same pressure signal. The fluid containing system may include an extracorporeal blood flow circuit, e.g. as part of a dialysis machine, and a cardiovascular system of a human patient.

31 Claims, 8 Drawing Sheets

(51) Int. Cl.
*B01D 61/30* (2006.01)
*B01D 61/32* (2006.01)
*G01L 19/00* (2006.01)
*A61B 5/021* (2006.01)
*A61B 5/00* (2006.01)

(52) U.S. Cl.
CPC ......... *A61B 5/7217* (2013.01); *A61M 1/3621* (2013.01); *A61M 1/3653* (2013.01); *A61M 1/3656* (2014.02); *B01D 61/30* (2013.01); *B01D 61/32* (2013.01); *G01L 19/00* (2013.01)

(58) Field of Classification Search
CPC ..... A61B 5/7217; A61M 1/36; A61M 1/3607; A61M 1/3621; A61M 1/3639; A61M 1/3653; A61M 1/3656; A61M 2205/3331; A61M 2230/04; A61M 2230/30; G01L 19/00; B01D 61/22; B01D 61/32; B01D 2311/14; B01D 61/30
USPC .... 210/90, 97, 645, 646; 600/485, 500, 501, 600/502; 604/5.01, 6.01, 6.09, 65, 67; 702/50, 66, 71, 72
See application file for complete search history.

(56) References Cited

U.S. PATENT DOCUMENTS

| | | | |
|---|---|---|---|
| 5,486,286 A * | 1/1996 | Peterson | A61M 1/16 210/321.65 |
| 5,649,536 A * | 7/1997 | Ogura | A61B 5/02116 600/493 |
| 6,083,172 A | 7/2000 | Baker, Jr. et al. | |
| 6,090,048 A * | 7/2000 | Hertz | A61M 5/16859 600/485 |
| 6,536,260 B2 | 3/2003 | Williams | |
| 6,741,887 B1 * | 5/2004 | Gleeson | A61B 5/044 345/6 |
| 7,250,025 B2 | 7/2007 | Nigroni et al. | |
| 9,442,036 B2 * | 9/2016 | Furmanski | A61M 1/3653 |
| 2004/0138538 A1 * | 7/2004 | Stetson | A61B 5/14551 600/310 |
| 2005/0010118 A1 * | 1/2005 | Toyoda | A61B 5/02 600/486 |
| 2006/0047201 A1 | 3/2006 | Eide | |
| 2006/0211942 A1 | 9/2006 | Hoctor et al. | |
| 2008/0004904 A1 * | 1/2008 | Tran | A61B 5/0006 705/2 |
| 2008/0091118 A1 * | 4/2008 | Georgopoulos | A61B 5/04008 600/544 |
| 2009/0069647 A1 | 3/2009 | McNames et al. | |
| 2011/0106466 A1 * | 5/2011 | Furmanski | A61M 1/3653 702/51 |

FOREIGN PATENT DOCUMENTS

| | | |
|---|---|---|
| WO | 2009/156174 | 12/2009 |
| WO | 2010/149726 | 12/2010 |

OTHER PUBLICATIONS

Prosecution history of U.S. Appl. No. 13/380,631 (now issued U.S. Pat. No. 9,433,356) filed Mar. 16, 2012.
Prosecution history of U.S. Appl. No. 14/129,087 (now issued U.S. Pat. No. 9,427,513) filed Apr. 11, 2014.
Prosecution history of U.S. Appl. No. 12/988,146 (now issued U.S. Pat. No. 8,718,957) filed Oct. 15, 2010.
Prosecution history of U.S. Appl. No. 13/000,856 (now issued U.S. Pat. No. 8,715,216) filed Dec. 22, 2010.
Prosecution history of U.S. Appl. No. 14/270,246 (now issued U.S. Pat. No. 9,383,288) filed May 5, 2014.
Prosecution history of U.S. Appl. No. 13/519,532, filed Sep. 12, 2012.
Prosecution history of U.S. Appl. No. 14/123,397, filed Dec. 2, 2013.
Prosecution history of U.S. Appl. No. 13/519,483, filed Sep. 13, 2012.
Prosecution history of U.S. Appl. No. 13/519,559, filed Sep. 12, 2012.
Prosecution history of U.S. Appl. No. 14/408,849, filed Dec. 17, 2014.
Prosecution history of U.S. Appl. No. 14/651,730, filed Jun. 12, 2015.
Prosecution history of U.S. Appl. No. 14/777,695, filed Sep. 16, 2015.
Prosecution history of U.S. Appl. No. 14/917,099, filed Mar. 7, 2016.
Prosecution history of U.S. Appl. No. 15/104,861, filed Jun. 15, 2016.

* cited by examiner

FILTERING OF A TIME-DEPENDENT PRESSURE SIGNAL

This application is the U.S. national phase of International Application No. PCT/EP2012/061765 filed 20 Jun. 2012 which designated the U.S. and claims priority to U.S. Patent Application Ser. No. 61/502,878 filed 30 Jun. 2011 and SE 1150604-5 filed 30 Jun. 2011, the entire contents of each of which are hereby incorporated by reference.

TECHNICAL FIELD

The present invention generally relates to processing of a time-dependent pressure signal obtained from a fluid containing system, and in particular to filtering of such a pressure signal for removal of a signal component originating from a specific pulse generator. The present invention is e.g. applicable in fluid containing systems for extracorporeal blood treatment.

BACKGROUND ART

The above-mentioned pressure signal contains both an information component, e.g. pressure variations representing heart pulses, and a disturbance component, e.g. pressure variation caused by a blood pump. It is a challenging task to extract the information component by removing the disturbance component. For this purpose, existing methods have for instance employed an additional pressure signal which only contains the disturbance component, which may be referred to as a "pump pressure profile".

One approach has been presented in WO2009/156175, in which the pump pressure profile is either directly subtracted from the pressure signal or used as input to an adaptive filter structure. The pump pressure profile is a predicted time resolved profile of pressure pulses from a dedicated pulse generator (e.g. a blood pump). The predicted profile has been either mathematically deduced or previously recorded under controlled circumstances, i.e. without influence from other sources in order to obtain a clean profile.

The prior art also comprises WO2010/066405, which proposes eliminating a pump disturbance in a pressure signal by subtracting a mathematically modelled pump contribution from the pressure signal. In an alternative approach, when the pump contribution is unknown, WO2010/066405 proposes repeatedly sampling pressure values at a time point when the pump contribution is known to be minimal and estimating an average heart pulse magnitude based on the standard deviation of the sampled pressure values. The latter technique is only able to generate an estimate of the average heart pulse magnitude, and provides neither information on the shape of the heart pulse, nor data on the magnitude or timing of individual heart pulses.

A field in which the present invention is relevant is extracorporeal blood treatment. In extracorporeal blood treatment, blood is taken out of a patient, treated and then reintroduced into the patient by means of an extracorporeal blood flow circuit. Generally, the blood is circulated through the circuit by one or more pumping devices. The circuit is connected to a blood vessel access of the patient, typically via one or more access devices, such as needles or catheters, which are inserted into the blood vessel access. Such extracorporeal blood treatments include hemodialysis, hemodiafiltration, hemofiltration, plasmapheresis, etc. For monitoring and analysing the behaviour of physiological pressure generators such as the heart or respiratory system, e.g. for monitoring a subject's heart pulse rate, blood pressure and also the condition of the blood vessel access (e.g. to identify so-called Venous Needle Dislodgement, VND), it is thus a desire to extract/isolate pressure data originating from such physiological pressure generators. Examples of such monitoring techniques are found in WO97/10013, WO2009/156174 and WO2010/149726.

However, existing solutions often require extensive memory and processing usage for processing the pressure signals, and they may also be unable to provide instantaneous information about the physiological pulses, such as magnitude, shape and timing. Some solutions also require known or predefined pump pressure profiles to filter the pressure signal. These pump pressure profiles may be difficult to obtain, may increase the complexity of implementation, and may generate unreliable results unless care is taken when measuring/calculating the pump pressure profiles.

Corresponding needs and tasks may arise in other fields of technology. Thus, generally speaking, there is a need for an improved technique for processing a time-dependent pressure signal obtained from a pressure sensor in a fluid containing system associated with a first pulse generator and a second pulse generator, in order to monitor a functional state or parameter of the fluid containing system by isolating a signal component originating from the second pulse generator among signal components originating from the first and second pulse generators. Specifically, the fluid containing system may comprise a first sub-system which comprises (or is associated with) the first pulse generator and the pressure sensor, a second sub-system which comprises (or is associated with) the second pulse generator, and a fluid connection between the first and second sub-systems.

SUMMARY

It is an object of the invention to at least partly fulfil one or more of the above-identified needs in view of the prior art.

One objective is to provide a technique that enables extraction of an information component in a pressure signal obtained in a fluid containing system, by removal or suppression of a disturbance component in the pressure signal.

Another objective is to provide such a technique that is simple to implement in a fluid containing system.

A further objective is to provide a filtering technique with an improved usage of processing or memory capacity.

Another objective is to provide a technique that enables monitoring of a property of the first subsystem, the second subsystem, or the integrity of the fluid connection between the two sub-systems in the above-mentioned fluid containing system.

Yet another objective is to provide such a technique capable of being used for monitoring of one or more properties of the cardiovascular system of a human subject.

One or more of these objectives, as well as further objectives that may appear from the description below, are at least partly achieved by means of devices, an apparatus for blood treatment, methods and a computer readable-medium according to the independent claims, embodiments thereof being defined by the dependent claims.

In its various aspects, the invention provides filtering techniques that are designed with knowledge about the pulse generation process in the first pulse generator. Specifically, the inventive filtering is based on the knowledge that the pressure signal includes consecutive pulse cycles, and that each pulse cycle has a known occurrence of first pulses, even if the shape of the first pulse(s) within the individual pulse cycle is unknown (e.g. depending on the operating conditions of the fluid containing system and the first pulse generator). As used herein, a "pulse cycle" is tied to the construction of the first pulse generator and is manifested as a repeating structure of a predetermined number of first pulses in the pressure signal. The second pulses are overlaid or superposed on the pulse cycles in the pressure signal. By relating each current data sample, obtained from the pressure signal, to a current pulse cycle, it is possible to generate an appropriate reference value for each current data sample by selecting and processing a set of preceding and/or subsequent data samples in the pressure signal for each current data sample. Based on this insight, the invention in its various aspects may be designed to generate each reference value such that the resulting time-sequence of reference values form an estimated temporal profile of the first pulse (s) within the current pulse cycle. Thereby, each reference value will represent an estimation of the instant signal contribution from the first pulse(s) within the current pulse cycle. By subtracting this instant signal contribution from the respective current data sample, a time-sequence of output samples can be generated for the current pulse cycle so as to be essentially free of first pulses.

It is to be noted that the inventive filtering is based on the presumption that the shape of the first pulses is approximately unchanged over a number of successive pulse cycles, so that it is possible to derive appropriate reference values for current data samples based on preceding and/or subsequent data samples. The inventive filtering also presumes that the first and second pulses are generated at different rates, so that the location of the second pulses differ between consecutive pulse cycles. Thereby, the resulting output samples will contain a signal contribution of second pulses, if present in the pressure signal, while the signal contribution of first pulses is eliminated or at least significantly suppressed.

In its various aspects, the inventive filtering is simple to implement in a fluid containing system, since it only requires a single pressure sensor. The inventive filtering obviates the complexity of obtaining a reference profile from another pressure sensor, as well as the complexity of using and possibly adapting this reference profile for appropriate filtering of the pressure signal, as suggested in the prior art. In comparison to prior art techniques, the inventive filtering also obviates the need to pre-record or pre-calculate reference profiles, the need to store these reference profiles, and the complexity of using such stored reference profiles for filtering of the pressure signal. Thus, the inventive filtering may improve usage of at least one of processing capacity and memory capacity.

In the claims, the inventive filtering is defined in terms of two different approaches, namely a cycle-synchronization (CS) approach and a proximity prediction (PP) approach. It should be emphasized that both of these approaches fall within the general inventive concept discussed in the foregoing.

A first aspect of the CS approach is a device for processing a time-dependent pressure signal obtained from a pressure sensor in a fluid containing system associated with a first pulse generator and a second pulse generator. The pressure sensor is arranged in the fluid containing system to detect first pulses originating from the first pulse generator and second pulses originating from the second pulse generator, wherein the first pulse generator operates in a sequence of pulse cycles, each pulse cycle resulting in at least one first pulse. The device comprises: an input for the pressure signal, and a signal processor connected to the input and configured to: repetitively obtain a current data sample within a current pulse cycle in the pressure signal; calculate, for each current data sample within the current pulse cycle, a reference value as a function of a cycle-synchronized data sample in one or more other pulse cycles in the pressure signal, the cycle-synchronized data sample being obtained to have a location in said one or more other pulse cycles that corresponds to a location of the current data sample in the current pulse cycle; and operate a subtraction algorithm on the current data sample, using said reference value obtained for the current data sample as input, so as to generate a current output sample which is essentially free of a signal component attributable to said at least one first pulse.

As used herein, the "other" pulse cycle denotes another pulse cycle than the current pulse cycle. Depending on implementation, the one or more other pulse cycles may be preceding or subsequent to the current pulse cycle in the pressure signal, or both. The use of subsequent pulse cycles generally requires some form of buffering of the data samples. In one embodiment, the signal processor is configured to calculate the reference value as a function of the cycle-synchronized data sample in an adjacent pulse cycle, e.g. an immediately preceding pulse cycle. The signal processor may be further configured to set the reference value equal to the cycle-synchronized data sample in the adjacent pulse cycle.

In one embodiment, the signal processor is configured to calculate the reference value as an aggregation of the cycle-synchronized data sample and one or more adjacent data samples to the cycle-synchronized data sample in an adjacent pulse cycle, e.g. an immediately preceding pulse cycle.

In one embodiment, the signal processor is configured to calculate the reference value as an aggregation of cycle-synchronized data samples in at least two other pulse cycles. The signal processor may be further configured to calculate the aggregation to include one or more adjacent data samples to each cycle-synchronized data sample in said at least two other pulse cycles.

In one embodiment, the signal processor is configured to calculate the aggregation as a summation of data samples. The signal processor may be further configured to apply a weight factor to each data sample in said summation. The signal processor may further comprise an adaptive filter configured to adaptively determine each weight factor based on a difference between the current data sample and the output sample.

In one embodiment, the signal processor is configured to calculate the aggregation recursively, by updating a preceding reference value, which corresponds to the reference value and is calculated in a preceding pulse cycle. The signal processor may be further configured to calculate the reference value as a function of the preceding reference value and a difference between the cycle-synchronized data sample in the preceding pulse cycle and the preceding reference value. Here, the difference is thus calculated between a cycle-synchronized data sample and a reference value obtained in the same preceding pulse cycle, which may be the immediately preceding pulse cycle.

In one implementation of the recursive embodiment, the device further comprises a Kalman filter, which is configured to receive the time sequence of current data samples obtained within the current pulse cycle as input and estimate a set of states that represent a time sequence of reference values in the current pulse cycle. In a corresponding practical implementation, the signal processor may be configured to calculate a difference value between the current data sample and the cycle-synchronized data sample; generate a weighted feedback value by applying a weight factor to a cycle-synchronized output sample which is obtained to have a location in one or more preceding pulse cycles that corresponds to a location of the current data sample within the current pulse cycle; and generate the current output sample as a sum of the difference value and the weighted feedback value, wherein the weight factor may be selected such that the signal processor implements said Kalman filter.

In one implementation of the recursive embodiment, as well as all other embodiments disclosed herein, the signal processor is configured to obtain the current data sample as a pressure value in the pressure signal.

In another implementation of the recursive embodiment, the signal processor is configured to obtain the current data sample as a difference between proximate (e.g. consecutive) pressure values in the pressure signal. Thereby, the recursive embodiment may be configured to account for drifts in the operation of the first pulse generator.

The following embodiments are not only applicable to the first aspect of the CS approach but also to the first aspect of the PP approach, as described further below.

In one embodiment, the signal processor is configured to obtain first data samples from the pressure signal and obtain each current data sample by interpolation among the first data samples with respect to a respective location within the current pulse cycle. This embodiment thus allows each current data sample to be generated with a well-defined location in the current pulse cycle, while relaxing the requirements on the data sampling equipment that generates the first data samples.

In one such embodiment, the signal processor is configured to obtain the current data sample in synchronization with the pulse cycles.

In one such embodiment, the device further comprises an input for a synchronization signal that represents the pulse cycles of the first pulse generator, and the signal processor is responsive to the synchronization signal in at least one of obtaining the current data sample, calculating the reference value, and operating the subtraction algorithm.

In one embodiment, the fluid containing system comprises an extracorporeal blood processing apparatus, a cardiovascular system of a human subject, and a fluid connection between the extracorporeal blood processing apparatus and the cardiovascular system, wherein the first pulse generator is associated with the extracorporeal blood processing apparatus and the second pulse generator is associated with the human subject.

In one embodiment, the signal processor is configured to repetitively obtain the current data sample and calculate the reference value so as to generate a time-sequence of reference values that form an estimated temporal profile of said at least one first pulse within the current pulse cycle.

In one embodiment, the signal processor is configured to operate the subtraction algorithm so as to generate a time-sequence of current output samples which form a temporal profile of the second pulse.

In one embodiment, the signal processor is configured to generate at least three output samples for each current pulse cycle.

In one embodiment, the first pulse generator comprises a peristaltic pump comprising a rotor with at least one roller, and wherein each pulse cycle corresponds to a full rotation of the rotor. In an alternative embodiment, the first pulse generator comprises a peristaltic pump comprising a rotor with a number of rollers, and wherein each full rotation of the rotor generates the same number of pulse cycles as the number of rollers.

A second aspect of the CS approach is a device for processing a time-dependent pressure signal obtained from a pressure sensor in a fluid containing system associated with a first pulse generator and a second pulse generator. The pressure sensor is arranged in the fluid containing system to detect first pulses originating from the first pulse generator and second pulses originating from the second pulse generator, wherein the first pulse generator operates in a sequence of pulse cycles, each pulse cycle resulting in at least one first pulse. The device comprises: means for repetitively obtaining a current data sample within a current pulse cycle in the pressure signal; means for calculating, for each current data sample in the current pulse cycle, a reference value as a function of a cycle-synchronized data sample in one or more other pulse cycles in the pressure signal, the cycle-synchronized data sample being obtained to have a location in said one or more other pulse cycles that corresponds to a location of the current data sample in the current pulse cycle; and means for operating a subtraction algorithm on the current data sample, using said reference value obtained for the current data sample as input, so as to generate a current output sample which is essentially free of a signal component attributable to said at least one first pulse.

A third aspect of the CS approach is an apparatus for blood treatment, comprising an extracorporeal fluid circuit configured to be connected in fluid communication with a vascular access of a human subject and operable to circulate blood from the cardiovascular system of the human subject through a blood processing device and back to the cardiovascular system, and a device of the first or second aspects.

A fourth aspect of the CS approach is a method of processing a time-dependent pressure signal obtained from a pressure sensor in a fluid containing system associated with a first pulse generator and a second pulse generator. The pressure sensor is arranged in the fluid containing system to detect first pulses originating from the first pulse generator and second pulses originating from the second pulse generator, wherein the first pulse generator operates in a sequence of pulse cycles, each pulse cycle resulting in at least one first pulse. The method comprises: repetitively obtaining a current data sample within a current pulse cycle in the pressure signal; calculating, for each current data sample within the current pulse cycle, a reference value as a function of a cycle-synchronized data sample in one or more other pulse cycles in the pressure signal, the cycle-synchronized data sample being obtained to have a location in said one or more other pulse cycles that corresponds to a location of the current data sample in the current pulse cycle; and operating a subtraction algorithm on the current data sample, using said reference value obtained for the current data sample as input, so as to generate a current output sample which is essentially free of a signal component attributable to said at least one first pulse.

A fifth aspect of the CS approach is a computer-readable medium comprising computer instructions which, when executed by a processor, cause the processor to perform the method of the fourth aspect.

Any one of the above-identified embodiments of the first aspect of the CS approach may be adapted and implemented as an embodiment of the above-identified second to fifth aspects of the CS approach.

A first aspect of the PP approach is a device for processing a time-dependent pressure signal obtained from a pressure sensor in a fluid containing system associated with a first pulse generator and a second pulse generator. The pressure sensor is arranged in the fluid containing system to detect first pulses originating from the first pulse generator and second pulses originating from the second pulse generator, wherein the first pulse generator operates in a sequence of pulse cycles, each pulse cycle resulting in at least one first pulse. The device comprises: an input for the pressure signal, and a signal processor connected to said input and configured to: repetitively obtain a current data sample within the current pulse cycle in the pressure signal; calculate, for each current data sample within the current pulse cycle, a reference value as an estimate of the current data sample, the estimate being calculated by prediction based on at least two data samples in proximity to the current data sample in the pressure signal; and operate a subtraction algorithm on the current data sample, using said reference value obtained for the current data sample as input, so as to generate a current output sample which is essentially free of a signal component attributable to said at least one first pulse.

Depending on implementation, the at least two data samples may be preceding and/or subsequent to the current data sample in the pressure signal. The use of subsequent data sample(s) generally requires some form of buffering of the data samples.

In one embodiment of the PP approach, the signal processor is configured to calculate the prediction by applying a weight factor to each of the at least two data samples. The signal processor may further comprise an adaptive filter configured to adaptively determine each weight factor based on a difference between the current data sample and the current output sample.

A second aspect of the PP approach is a device for processing a time-dependent pressure signal obtained from a pressure sensor in a fluid containing system associated with a first pulse generator and a second pulse generator. The pressure sensor is arranged in the fluid containing system to detect first pulses originating from the first pulse generator and second pulses originating from the second pulse generator, wherein the first pulse generator operates in a sequence of pulse cycles, each pulse cycle resulting in at least one first pulse. The device comprises: means for repetitively obtaining a current data sample within the current pulse cycle in the pressure signal; means for calculating, for each current data sample within the current pulse cycle, a reference value as an estimate of the current data sample, the estimate being calculated by prediction based on at least two data samples in proximity to the current data sample in the pressure signal; and means for operating a subtraction algorithm on the current data sample, using said reference value obtained for the current data sample as input, so as to generate a current output sample which is essentially free of a signal component attributable to said at least one first pulse.

A third aspect of the PP approach is an apparatus for blood treatment, comprising an extracorporeal fluid circuit configured to be connected in fluid communication with a vascular access of a human subject and operable to circulate blood from the cardiovascular system of the human subject through a blood processing device and back to the cardiovascular system, and a device of the first or second aspects.

A fourth aspect of the PP approach is a method of processing a time-dependent pressure signal obtained from a pressure sensor in a fluid containing system associated with a first pulse generator and a second pulse generator. The pressure sensor is arranged in the fluid containing system to detect first pulses originating from the first pulse generator and second pulses originating from the second pulse generator, wherein the first pulse generator operates in a sequence of pulse cycles, each pulse cycle resulting in at least one first pulse. The method comprises: repetitively obtaining a current data sample within a current pulse cycle in the pressure signal; calculating, for each current data sample within the current pulse cycle, a reference value as an estimate of the current data sample, the estimate being calculated by prediction based on at least two data samples in proximity to the current data sample in the pressure signal; and operating a subtraction algorithm on the current data sample, using said reference value obtained for the current data sample as input, so as to generate a current output sample which is essentially free of a signal component attributable to said at least one first pulse.

A fifth aspect of the PP approach is a computer-readable medium comprising computer instructions which, when executed by a processor, cause the processor to perform the method of the fourth aspect.

Any one of the above-identified embodiments of the first aspect of the PP approach may be adapted and implemented as an embodiment of the above-identified second to fifth aspects of the PP approach.

Still other objectives, features, aspects and advantages of the present invention will appear from the following detailed description, from the attached claims as well as from the drawings.

BRIEF DESCRIPTION OF THE DRAWINGS

Exemplifying embodiments of the invention will now be described in more detail with reference to the accompanying schematic drawings.

DETAILED DESCRIPTION OF EXEMPLIFYING EMBODIMENTS

In the following, exemplifying embodiments of the invention will be described with reference to fluid containing systems in general. Thereafter, the embodiments and implementations of the invention will be further exemplified in the context of systems for extracorporeal blood treatment.

Throughout the following description, like elements are designated by the same reference signs.

General

Figure 1:
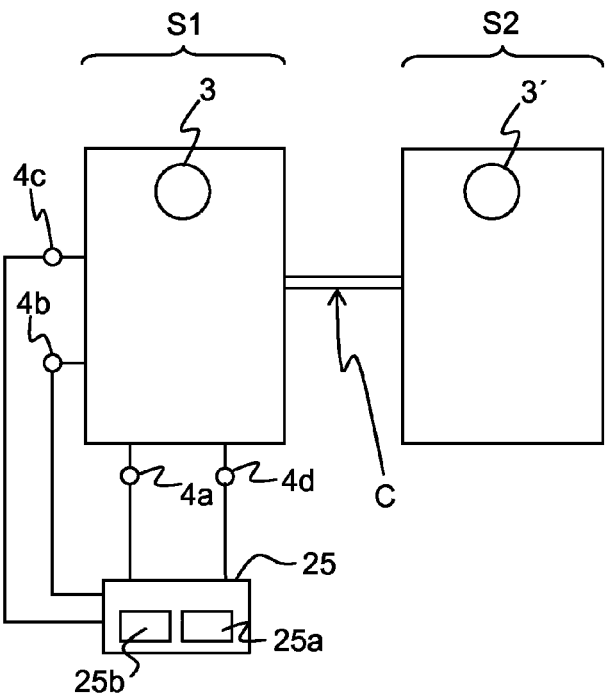
FIG. 1 is a schematic view of a general fluid containing system in which the inventive data processing may be used for filtering a pressure signal.

FIG. 1 illustrates a fluid containing system in which a fluid connection C is established between a first fluid containing sub-system S1 and a second fluid containing sub-system S2. The fluid connection C may or may not transfer fluid from one sub-system to the other. A first pulse generator 3 is arranged to generate a series of pressure waves in the fluid within the first sub-system S1, and a second pulse generator 3' is arranged to generate a series of pressure waves in the fluid within the second sub-system S2. A pressure sensor 4a is arranged to measure the fluid pressure in the first sub-system S1. Pressure waves generated by the second pulse generator 3' will travel from the second sub-system S2 to the first sub-system S1, via the connection C, and thus second pulses (waveforms) originating from the second pulse generator 3' will be detected by the pressure sensor 4a in addition to first pulses (waveforms) originating from the first pulse generator 3. It is to be noted that either one of the first and second pulse generators 3, 3' may include more than one pulse-generating device. Further, any such pulse-generating device may or may not be part of the respective sub-system S1, S2.

The system of FIG. 1 further includes a surveillance device 25 which is connected to one or more of the pressure sensors 4a, 4b, 4c, 4d as indicated in FIG. 1. Thereby, the surveillance device 25 acquires one or more pressure signals that are time-dependent to provide a real time representation of the fluid pressure in the first sub-system S1.

Generally, the surveillance device 25 is configured to monitor a functional state or functional parameter of the fluid containing system by isolating and analysing one or more second pulses in one of the pressure signals. The functional state or parameter may be monitored for various characteristics of the second sub-system S2. If the second sub-system S2 is a human subject, as described further below, the functional state or parameter may be monitored for assessing heart pulse rate or blood pressure of the human subject. Additionally, as will be further exemplified in the following, the functional state or parameter may be monitored to identify a fault condition, e.g. in the first or second sub-systems S1, S2, the second pulse generator 3' or the fluid connection C. Upon identification of a fault condition, the surveillance device 25 may issue an alarm or warning signal and/or alert a control system of the first or second sub-systems S1, S2 to take appropriate action. Alternatively or additionally, the surveillance device 25 may be configured to store or output (e.g. for display) a time sequence of values of the functional state or parameter.

Depending on implementation, the surveillance device 25 may use digital components or analog components, or a combination thereof, for receiving and processing the pressure signal. The device 25 may be a computer, or a similar data processing device, with adequate hardware for acquiring and processing the pressure signal in accordance with different embodiments of the invention. Embodiments of the invention may e.g. be implemented by software instructions that are supplied on a computer-readable medium for execution by a processor 25a in conjunction with an electronic memory 25b in the device 25.

Typically, the surveillance device 25 is configured to repeatedly process the time-dependent pressure signal(s) to isolate the second pulses, if present in the pressure signal. This processing is schematically depicted in the flow chart of FIG. 2.

Figure 2:
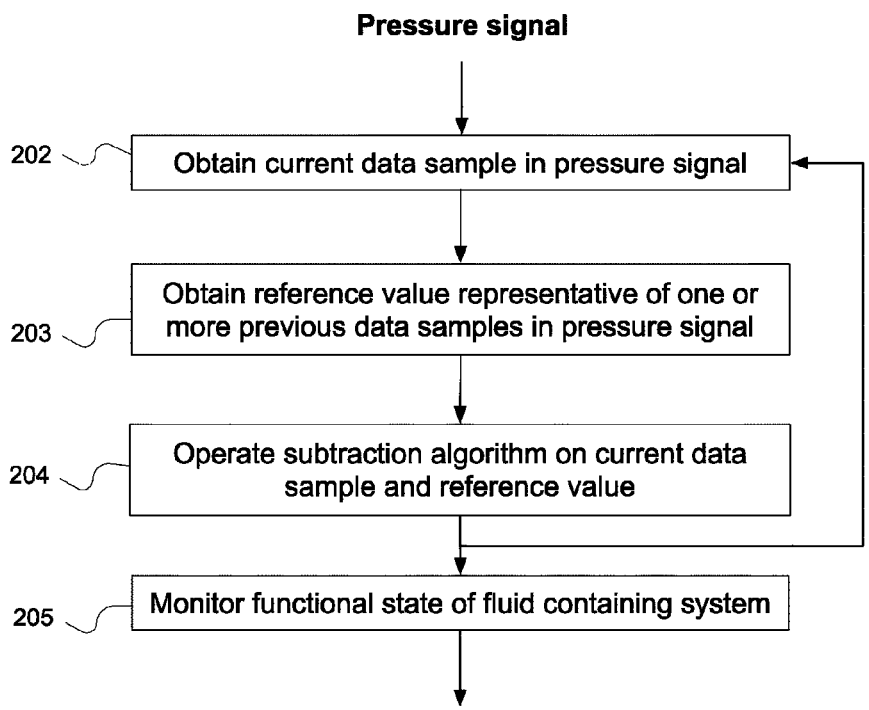
FIG. 2 is a flow chart for an embodiment of an inventive filtering process.

The process in FIG. 2 operates on a time-dependent pressure signal which is measured by e.g. the pressure sensor 4a in the fluid containing system of FIG. 1, which is associated with the first pulse generator 3 and the second pulse generator 3'. As noted above, the pressure signal is processed in order to monitor a functional state or parameter of the fluid containing system by isolating a signal component originating from the second pulse generator 3' among signal components originating from the first and second pulse generators 3, 3'. The processing involves a step 202 of obtaining a current data sample from the pressure signal, and a step 203 of obtaining a reference value representative of at least one preceding data sample in the pressure signal. In a step 204, a subtraction algorithm is operated on the current data sample, using the reference value as input, so as to essentially eliminate any signal component attributable to the first pulse (first pulse contribution). The result of step 204 is an output sample which is essentially free of the signal component attributable to the first pulse. By "essentially free" is meant that the first pulse contribution is removed from the pressure signal to such an extent that any signal contribution from second pulses may be detected and analysed for the purpose of monitoring the aforesaid functional state or parameter. The steps 202-204 are repeated at consecutive time steps, whereby step 202 is advanced one time step in the pressure signal for each repetition. In one implementation, the incoming pressure signal is digital and formed by a time sequence of data samples, where the steps 202-204 may, but need not, be repeated for every data sample in the pressure signal. In another implementation, the incoming pressure signal is analogue, and the steps 202-204 comprises an initial analog-to-digital conversion for extraction of the current data sample from the pressure signal. Alternatively, steps 202-204 may implement an analog process, in which a pressure value in the pressure signal at a selected time point forms the current data sample. Irrespective of implementation, the process in FIG. 2 operates on a sequence of data samples in the pressure signal and generates a corresponding sequence of output samples. To the extent that the pressure signal contains both first and second pulses, the sequence of output samples includes the one or more second pulses, or part thereof, which may be evaluated for various characteristics in a step 205 for monitoring a functional state or functional parameter of the fluid containing system.

Introduction to Inventive Concept

As indicated in FIG. 2, the reference value is representative of at least one preceding data sample in the pressure signal. The "preceding data sample" is thus an earlier data sample, relative to the current data sample, in the pressure signal. The preceding data sample may, e.g., be located immediately preceding the current data sample or one or more pulse cycles previously. A "pulse cycle" or "cycle" is defined in relation to the operation of the first pulse generator 3, and each cycle contains at least one first pulse. It should be noted that the definition of a cycle may be somewhat arbitrary, and a cycle may contain any number of first pulses, as long as each first pulse has a known and/or predictable location within the cycle. In one example, the first generator is a peristaltic pump, and the cycle may represent one complete pump member revolution or a partial pump member revolution corresponding to a rotor angle interval (cf. rotor 30 of pump 3 in FIG. 4). A peristaltic pump may comprise any number of rollers, although a typical number is two or three. In the following examples, which are based on peristaltic pumps with two rollers, each cycle is defined as a full revolution (360 degrees) of the rotor and its rollers and comprises two first pulses, each pulse being generated when one of the two rollers engages a tube segment to push fluid through the tube segment, as is well-known to the skilled person. Although the rollers may be distributed evenly around a circle and symmetries could be used to divide a complete roller rotation into cycles between each roller, manufacturing and design differences may render it advantageous to use a complete pump member rotation rather than to rely on symmetries. However, if balanced rollers can been assumed, the cycle may be defined to include a single first pulse, such that consecutive cycles are associated with different rollers.

As used herein, a preceding data sample which has the same, or at least closely similar, timing within the cycle as the current data sample is denoted a "cycle-synchronized data sample". Stated otherwise, a cycle-synchronized data sample has a relative location in a preceding cycle that corresponds to the relative location of the current data sample in a current cycle.

The reference value may be an averaged value, possibly weighted, of two or more immediately preceding samples, or of two or more cycle-synchronized data samples, which thus may be obtained from two or more preceding cycles. In the following examples, the cycle-synchronized data samples are taken from one or more immediately preceding cycles. However, in principle, the cycle-synchronized samples may be taken from any preceding cycle(s), although greater accuracy may be achieved by using the cycle(s) closest in time to the current data sample, since it is likely that the these cycle(s) are generated at similar operational conditions as the current cycle, e.g. with respect to pumping rate, average fluid pressure, compliance volumes, pump occlusion, etc. In the examples described below, the reference value is generated based on cycle-synchronized samples taken from preceding cycle(s) with a fixed and predetermined relation to the current cycle. However, in a variant, a selection mechanism may be implemented to dynamically select the preceding cycle(s) to be used for obtaining the cycle-synchronized samples, e.g. by comparing the operational conditions (pumping rate, average fluid pressure, etc) of the current cycle to each of a set of preceding cycles. The dynamic selection of preceding cycle(s) may be simply implemented by dynamically setting a weight factor for each cycle-synchronized sample when calculating the average value (cf. the filter structures in FIGS. 9, 10, 11 and 12).

Figure 5A:
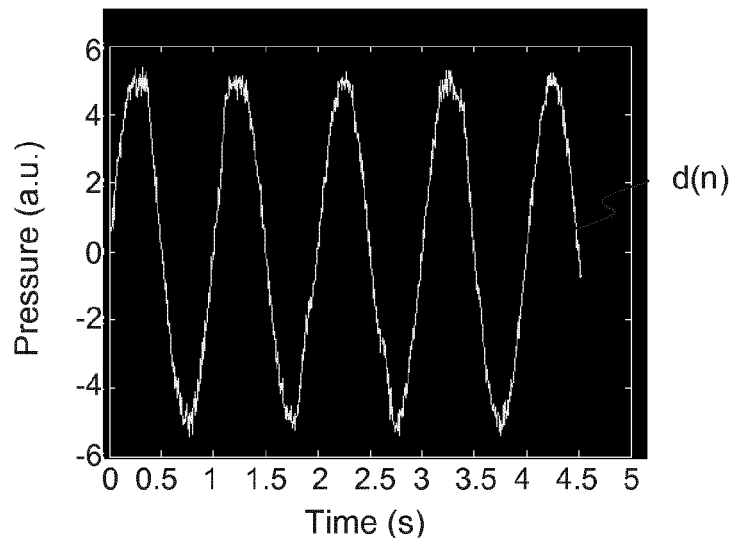
FIG. 5A is a plot of a pressure signal as a function of time.
Figure 5B:
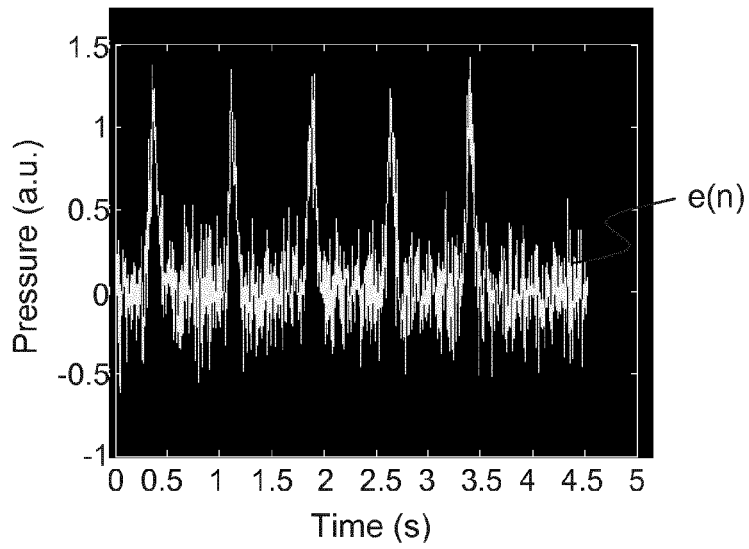
FIG. 5B is a plot of the pressure signal after filtering.

The effectiveness of the inventive filtering is exemplified in FIG. 5, in which FIG. 5A shows an example of a time-dependent pressure signal d(n) containing first and second pulses with a relative magnitude of 10:1. The first and second pulses have a frequency of 1 Hz and 1.33 Hz, respectively. Due to the difference in magnitude, the pressure signal is dominated by the first pulses. FIG. 5B shows the time-dependent filtered signal e(n) that is obtained after applying the inventive filtering technique to the pressure signal d(n). The filtered signal e(n) is made up of second pulses and noise. It should be noted that there is an absence of second pulses after about 4 seconds, which may be observed by the surveillance device (25 in FIG. 1) and identified as a fault condition of the fluid containing system, e.g. a disruption of the fluid connection C.

In the following, exemplifying embodiments for estimating or generating the first pulse contribution (pump pulse contribution) at a given time and for extracting second (physiological) pulses of a pressure signal will be explained.

Figure 3A:
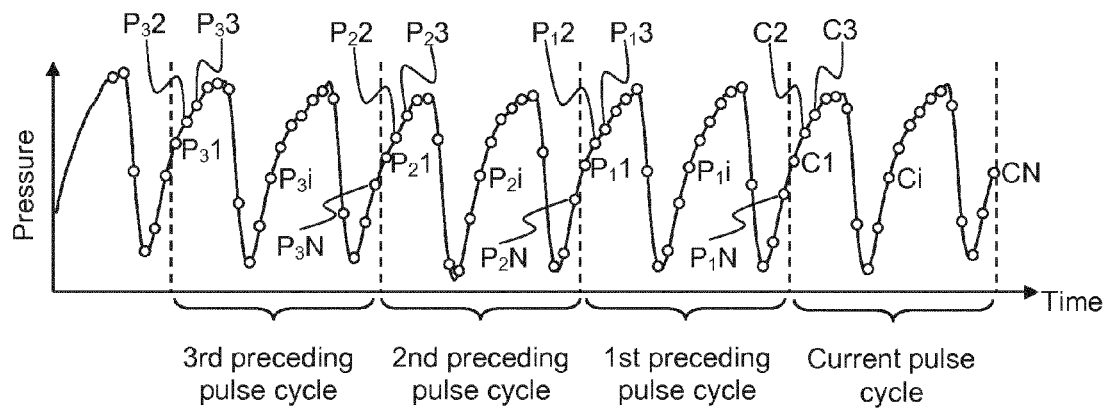
FIG. 3A is a plot of a pressure signal with selected data samples indicated.

FIG. 3A illustrates an example of a time-dependent pressure signal measured by the pressure sensor 4a in FIG. 1. The pressure signal comprises superimposed contributions from the first pulse generator 3 and the second pulse generator 3', where the first pulse generator 3 dominates the shape of the pressure signal. Along the signal, a number of samples have been indicated with e.g. C1, C2, C3, etc for current data samples, $P_1 1$, $P_1 2$, $P_1 3$ for cycle-synchronized data samples in a first preceding pulse cycle, $P_2 1$, $P_2 2$, $P_2 3$ for cycle-synchronized data samples in a second preceding pulse cycle, etc. N represents the number of data samples in each pulse cycle. The indicated data samples will be explained in connection with FIGS. 3B-3H in the following. Furthermore, the pressure signal has been subdivided into a number of consecutive sections corresponding to durations of consecutive pulse cycles of the first pulse generator 3. In the illustrated examples, the first pulse generator 3 is a peristaltic pump with two rollers, and each pulse cycle is defined to comprise two first pulses. As explained above, each pulse cycle thereby corresponds to a full rotation of the rotor. The pulse cycles have been denoted a current pulse cycle, a first preceding pulse cycle, a second preceding pulse cycle and a third preceding pulse cycle. Any number of preceding pulse cycles may be used, although only three are shown for simplicity.

Figure 3B:
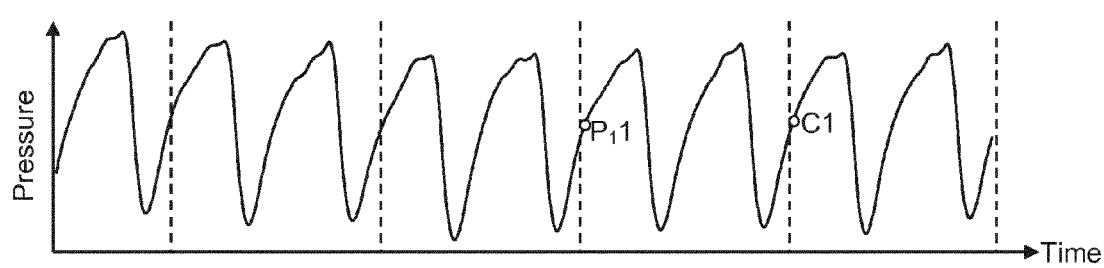
FIGS. 3B-3H show sub-sets of the data samples of FIG. 3A for the purpose of exemplifying different embodiments of the present invention.

Example I. Reference Value Based on a Corresponding Cycle-Synchronized Sample of the Immediately Preceding Pulse Cycle FIG. 3B illustrates a first example where a reference value is obtained based on a corresponding cycle-synchronized sample of the immediately preceding pulse cycle. FIG. 3B shows a current data sample C1 from a first position in the current pulse cycle and one preceding cycle-synchronized data sample $P_1 1$ from a first position in the first preceding pulse cycle corresponding to the relative location of the current data sample in the current pulse cycle. In the example with a peristaltic pump, the cycle-synchronized data sample $P_1 1$ has been obtained at an instance in time corresponding to one full rotation earlier of the rotor, i.e. 360 degrees earlier.

Figure 6:
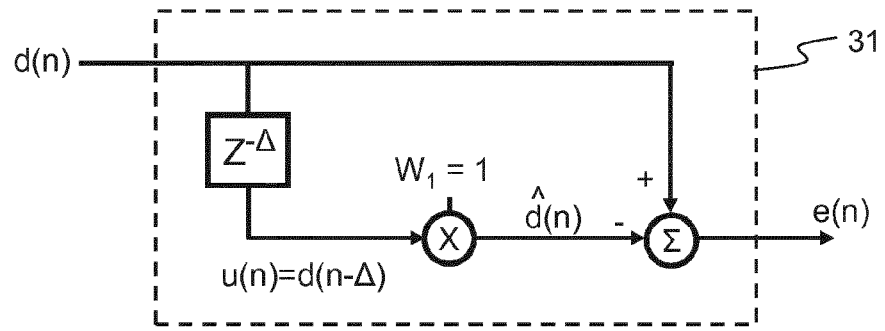
FIGS. 6-14 are schematic views of filter structures according to different embodiments of the present invention.

FIG. 6 is a schematic diagram of a filter structure 31 that implements the process in FIG. 2 to achieve the data processing indicated in FIG. 3B. In FIG. 6, a block $Z^{-\Delta}$ is included to implement a step of obtaining, in the pressure signal, a preceding data sample u(n) with a suitable negative delay $(-\Delta)$ to a current data sample d(n). The delay is suitably selected such that the preceding data sample u(n) is a cycle-synchronized data sample. In the illustrated example, $\Delta$ is set to a time value corresponding to 360°. The preceding data sample is multiplied in the multiplication block X with a weight factor $W_1$ which generates the reference value $\hat{d}(n)$, here by directly using the preceding data sample (indicated by a weight factor $W_1$ being set to 1). The resulting reference value $\hat{d}(n)$ is input to a summation block $\Sigma$ that performs the subtraction (step 204 in FIG. 2) of the reference value $\hat{d}(n)$ from the current data sample d(n) to generate the output sample e(n). Thus, in FIG. 6, a subtraction algorithm is operated on a current data sample C1, using the preceding data sample $P_1 1$ as a reference value, to generate an output sample which is essentially free of a signal component attributable to the first pulse.

The sequence of output samples generated as the process in FIG. 3B is repeated for a sequence of consecutive current data samples, will however generally not be a true representation of the second pulse, since the second pulse typically is present, at least partly, in both the current pulse cycle and the preceding pulse cycle but at different locations (since the first and second pulses generally are generated at different rates). Therefore, the sequence of output samples generates a filtered signal that comprises (the part of) the second pulse in the current pulse cycle and a negative version of (the part of) the second pulse in the preceding cycle, i.e. the latter is overlaid on the former but with reversed sign and delayed one complete first pulse generator cycle.

It is to be understood that the filter structure 31 in FIG. 6, as well as the filter structures 31 in FIGS. 7-12 to be described below, are given to conceptually explain different embodiments. Thus, the functions of applying a negative delay and generate the reference value may be implemented by the signal processor (25a in FIG. 1) while repeatedly executing steps 202-204 of the process in FIG. 2, such that the reference value is generated during one iteration of steps 202-204 and stored in electronic memory (cf. 25b in FIG. 1)

and retrieved from the electronic memory in a subsequent iteration of steps 202-204. It is also possible to use a combination of electronic components that creates actual delayed versions of the signal.

Figure 3C:
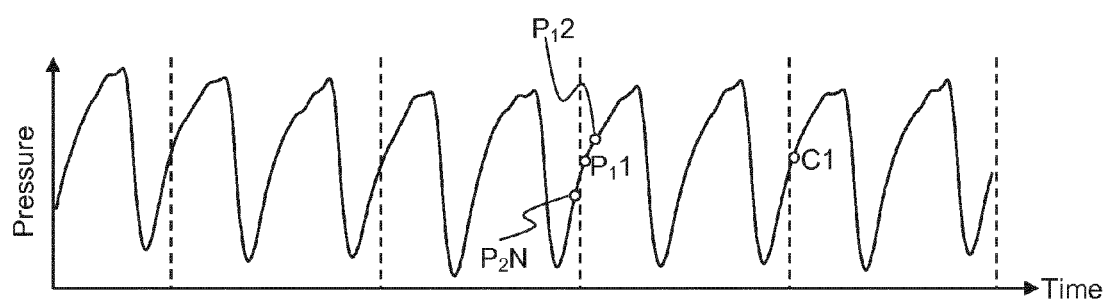

FIG. 3C illustrates a variation of the first example where the reference value is calculated as an aggregation ("neighbourhood aggregation") of the cycle-synchronized data sample $P_1 1$ and two adjacent data samples $P_1 2$ and $P_2 N$ to the cycle-synchronized data sample in the immediately preceding pulse cycle. The neighbourhood aggregation may yield a better approximation of the reference value and describes a combination of data samples and may involve a weighted or non-weighted summation of the data samples, e.g. an averaging of $P_1 1$, $P_1 2$ and $P_2 N$.

Figure 7:
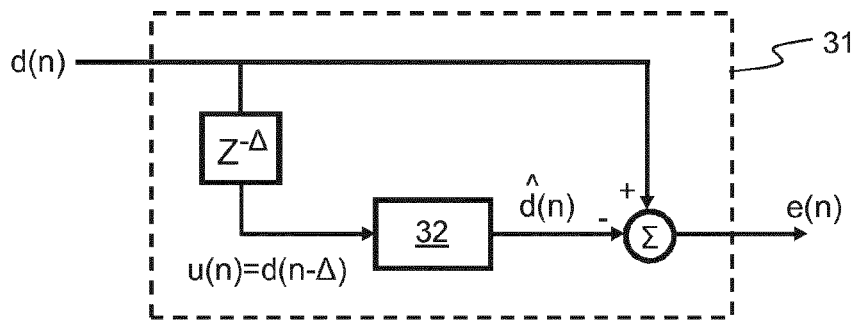

FIG. 7 is a schematic diagram of a filter structure 31 similar to that of FIG. 6, where the multiplication block X which is implemented to generate the reference value has been replaced by an aggregation block 32 ("filter") that implements the neighbourhood aggregation, e.g. by summation, possibly involving weight factors which may be set individually to achieve an improved reference value. Although FIG. 7 indicates that the aggregation block 32 receives individual cycle-synchronized data samples, it is realized that the aggregation block 32 may be configured to process the incoming stream of cycle-synchronized data samples so as to generate the reference value $\hat{d}(n)$ for each current data sample $d(n)$ by aggregation of the cycle-synchronized value (of the current data sample) with adjacent data samples, on one or both sides of the cycle-synchronized value.

Figure 8:
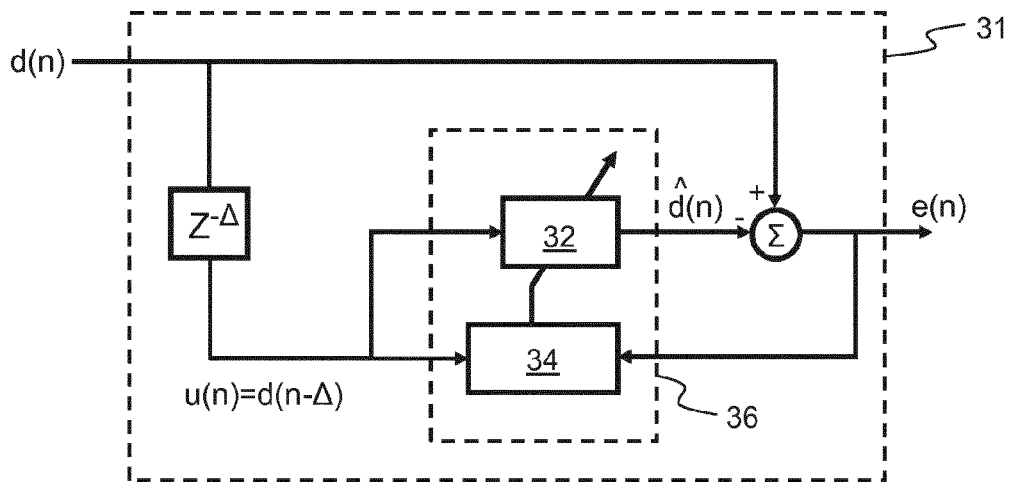

FIG. 8 is a schematic diagram of a filter structure 31 similar to that of FIG. 7, where the aggregation block 32 has been supplemented by an adaptive block 34 configured to adaptively determine each weight factor based on the cycle-synchronized sample $u(n)$ and the output sample $e(n)$. The aggregation block 32 and the adaptive block 34 define an adaptive filter indicated by 36. The algorithm of the adaptive block 34 may be configured to automatically and adaptively adjust the weight factors of the aggregation block 32 to achieve a best-fit for the approximated reference value $\hat{d}(n)$ so as to minimize or otherwise optimize the output sample $e(n)$. Adaptive algorithms include for instance the Recursive Least Square (RLS) method and the Least Mean Square (LMS) method.

Figure 3D:
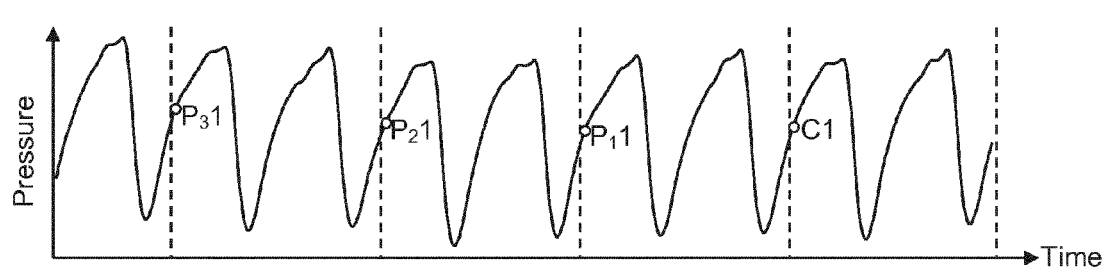

Example II. Reference Value Based on Corresponding Cycle-Synchronized Samples of Multiple Preceding Pulse Cycles FIG. 3D illustrates a second example with corresponding cycle-synchronized samples of multiple preceding pulse cycles used for obtaining the reference value. FIG. 3D shows a first current data sample C1 from a first position in the current pulse cycle and first, second and third preceding cycle-synchronized data samples $P_1 1$, $P_2 1$ and $P_3 1$ from positions in the first, second and third preceding pulse cycles corresponding to the location of the first current data sample in the first current pulse cycle. The reference value is calculated as an aggregation of the first, second and third data samples $P_1 1$, $P_2 1$ and $P_3 1$. A subtraction algorithm is operated on the current data sample, using the reference value, to generate an output sample which is essentially free of a signal component attributable to the first pulse.

Figure 3E:
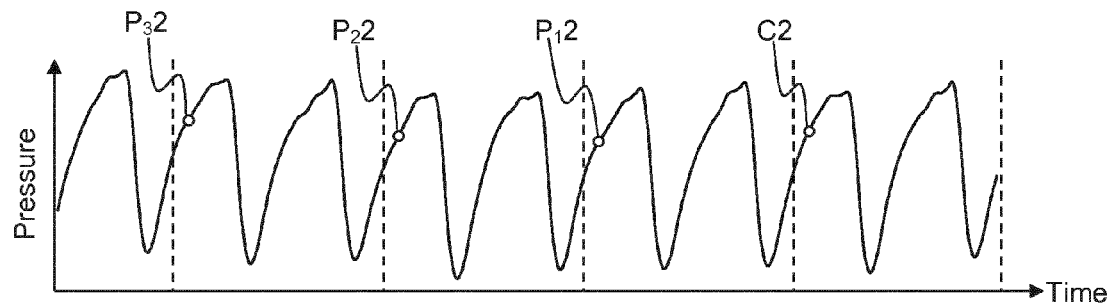
Figure 3F:
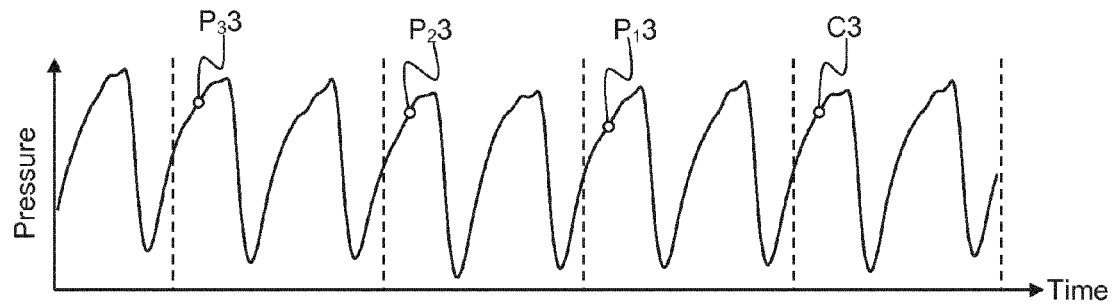

The procedure is repeated for current sample C2 and its cycle-synchronized data samples $P_1 2$, $P_2 2$ and $P_3 2$ shown in FIG. 3E, for current sample C3 and its cycle-synchronized data samples $P_1 3$, $P_2 3$ and $P_3 3$ shown in FIG. 3F, and so on.

In the example with a peristaltic pump, the first preceding cycle-synchronized data sample $P_1 1$, $P_1 2$ and $P_1 3$, respectively (cf. FIGS. 3D-3F), has been obtained at an instance in time corresponding to one full rotation earlier of the rotor, i.e. 360 degrees earlier.

Figure 9:
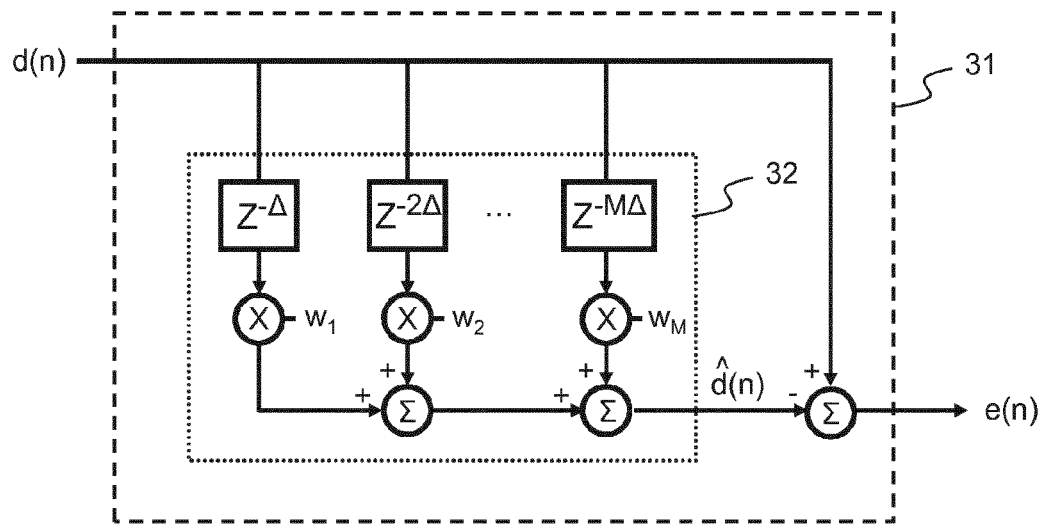

FIG. 9 is a schematic diagram of a filter structure 31 that implements the process in FIG. 2 to achieve the data processing indicated in FIGS. 3D-3F. In FIG. 9, blocks $Z^{-\Delta}$, $Z^{-2\Delta}$ to $Z^{-M\Delta}$ are included in an aggregation block 32 and configured to obtain, in the pressure signal, preceding data samples with suitable negative delays $(-\Delta)$, $(-2\Delta)$ to $(-M\Delta)$ to the current data sample $d(n)$. The delays are suitably selected such that the preceding data samples are cycle-synchronized data samples. In the illustrated example, $\Delta$ is set to a time value corresponding to 360°. Each preceding data sample is multiplied in the multiplication blocks X with a respective weight factor ($W_1$ to $W_M$) and added together by the summation blocks $\Sigma$ to generate the reference value $\hat{d}(n)$. The resulting reference value $\hat{d}(n)$ is input to a downstream summation block $\Sigma$ that implements the subtraction (step 204 in FIG. 2) of the reference value $\hat{d}(n)$ from the current data sample $d(n)$ to generate the output sample $e(n)$. Thus, in FIG. 9, a subtraction algorithm is operated on a current data sample, e.g. C1, using an aggregation of the preceding data samples, e.g. $P_1 1$, $P_2 1$ and $P_3 1$ if M=3, as a reference value, to generate an output sample which is essentially free of a signal component attributable to the first pulse.

Figure 13:
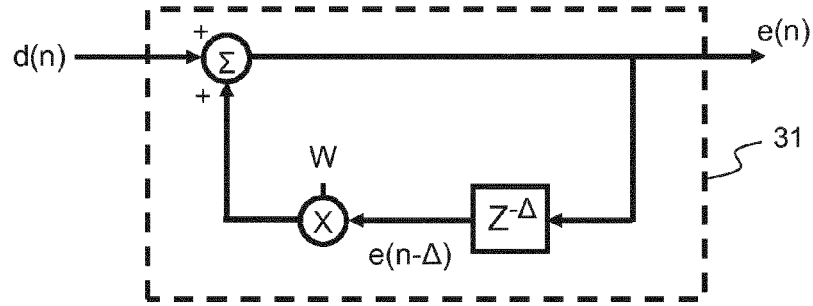

The filter structure 31 in FIG. 9 may be implemented as a feedback loop if the respective weight factor $W_i$ (i=1 to M) is set to $-W^i$ (with $|W|<1$) and if $M \rightarrow \infty$. A filter structure 31 with such a feedback loop is shown in FIG. 13, in which the cycle-synchronized output sample $e(n-\Delta)$ of a preceding cycle (generated by block $Z^{-\Delta}$) is added to the current data sample $d(n)$ in a summation block $\Sigma$, after applying the weight factor W to the cycle-synchronized output sample $e(n-\Delta)$ in a multiplication block X. While being simple to implement, such a feedback loop has the drawback of requiring a fixed relation between the weights of the different cycles. Analogous to a cycle-synchronized data sample, a "cycle-synchronized output sample" has been calculated for a relative location in the preceding cycle that corresponds to the relative location of the current data sample in the current cycle.

Figure 10:
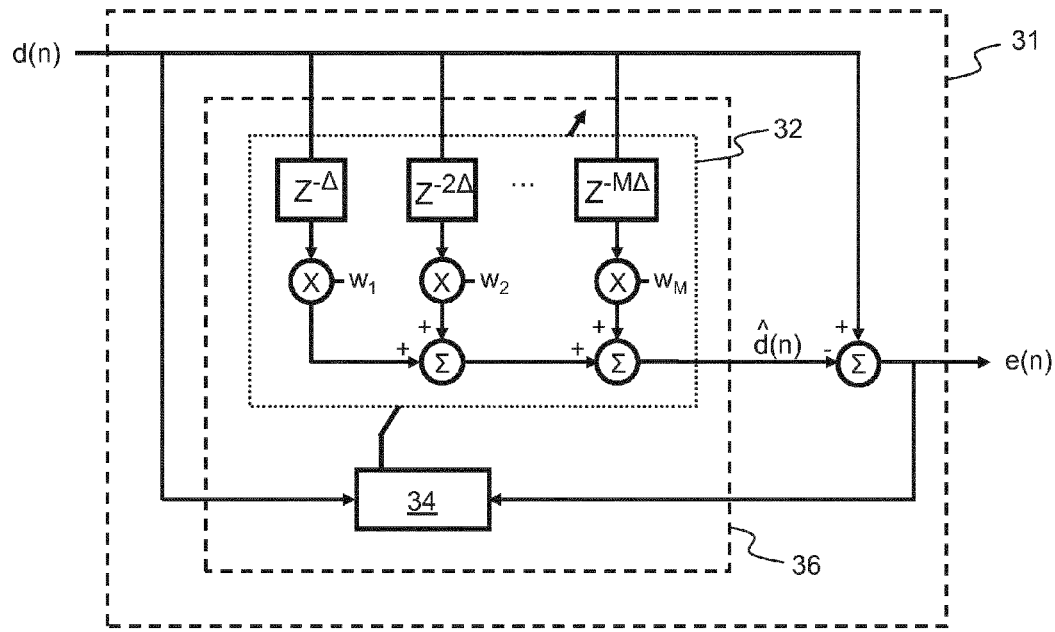

FIG. 10 is a schematic diagram of a filter structure 31 similar to that of FIG. 9, where the aggregation block 32 has been supplemented by an adaptive block 34 that implements an adaptive function configured to adaptively determine the weight factors $W_1$ to $W_M$ of the aggregation block 32 to achieve a best-fit for the approximated reference value $\hat{d}(n)$. The adaptive block 34 may be configured as described in relation to FIG. 8.

Figure 3G:
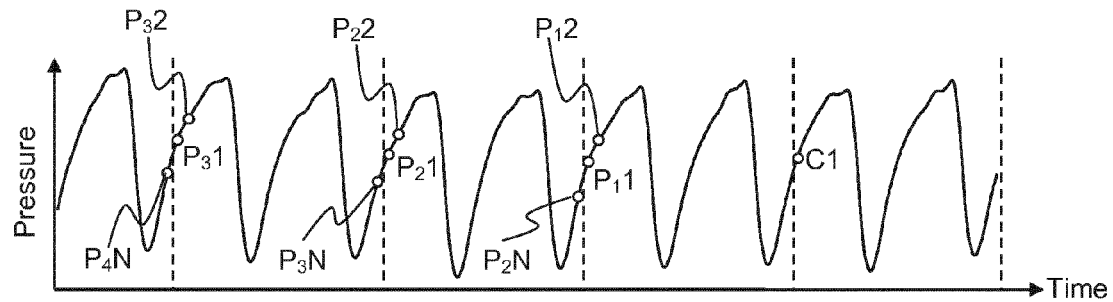

FIG. 3G illustrates a variation of the second example where the reference value is calculated as an aggregation of the cycle-synchronized data samples $P_1 1$, $P_2 1$ and $P_3 1$, each in turn aggregated (by neighbourhood aggregation) with two adjacent data samples $P_1 2$ and $P_2 N$; $P_2 2$, $P_3 N$; and $P_3 2$, $P_4 N$ respectively. Hence, this variation represents a combination of the example in FIG. 3C involving adjacent data samples, and the example in FIGS. 3D-3F involving cycle-synchronized samples of multiple preceding pulse cycles.

Figure 11:
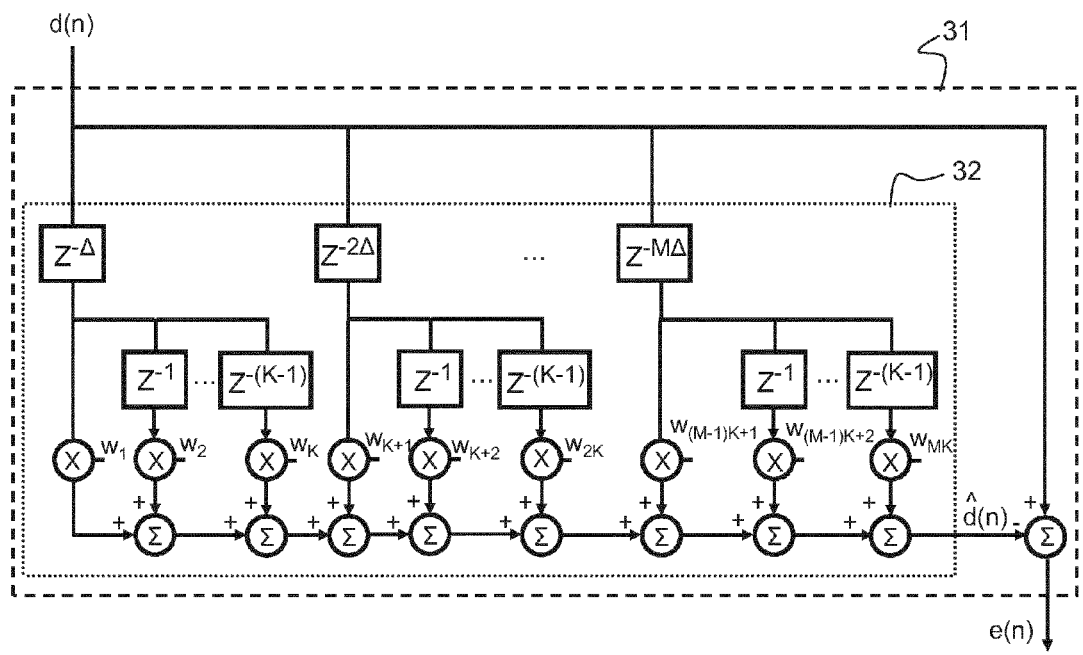

FIG. 11 is a schematic diagram of a filter structure 31 that implements the process in FIG. 2 to achieve the data processing indicated in FIG. 3G. In FIG. 11, the aggregation block 32 is configured to aggregate preceding (cycle-synchronized) data samples, which are obtained by blocks $Z^{-\Delta}$, $Z^{-2\Delta}$ to $Z^{-M\Delta}$ with suitable negative delays $(-\Delta)$, $(-2\Delta)$ to $(-M\Delta)$, and respective adjacent data samples, which are obtained by blocks $Z^{-1}$ to $Z^{-(K-1)}$. The preceding data samples are aggregated using the summation blocks $\Sigma$ while applying weight factors $W_1$ to $W_{MK}$. The resulting reference value $\hat{d}(n)$ is input to a downstream summation block $\Sigma$ that performs the subtraction (step 204 in FIG. 2) of the reference value $\hat{d}(n)$ from the current data sample $d(n)$ to generate the output sample $e(n)$. Like in FIG. 7, the aggregation block 32 in FIG. 11 may be configured to process the incoming stream of cycle-synchronized data samples so as to generate the reference value $\hat{d}(n)$ for each current data sample $d(n)$ by aggregation of the cycle-synchronized value (of the current data sample) with adjacent data samples, on one or both sides of the cycle-synchronized value. Thus, with reference to FIG. 3C, the filter structure 31 in FIG. 11 may operate a subtraction algorithm on a current data sample C1, using an aggregation of the neighbourhood aggregated preceding data samples around $P_11$, $P_21$ and $P_31$ as a reference value, to generate an output sample which is essentially free of a signal component attributable to the first pulse.

Figure 12:
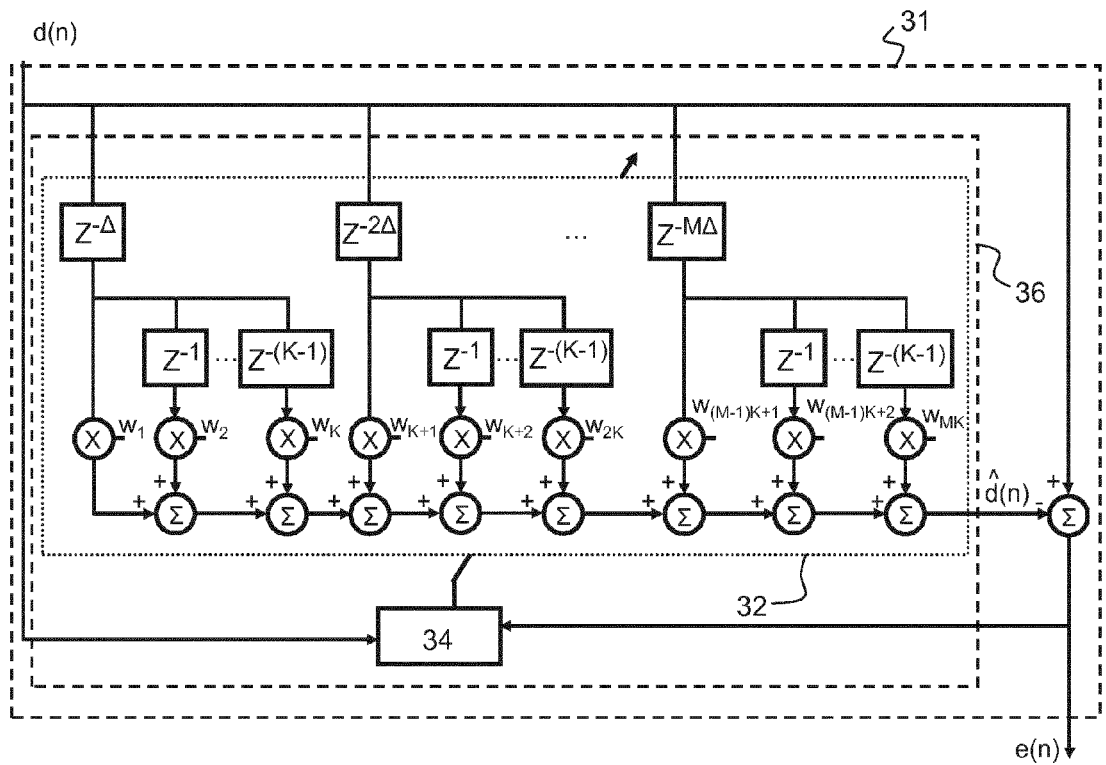

FIG. 12 is a schematic diagram of a filter structure 31 similar to that of FIG. 11, where the aggregation block 32 has been supplemented by an adaptive block 34 that implements an adaptive function configured to determine the weight factors $W_1$ to $W_{MK}$ of the aggregation block 32 to achieve a best-fit for the approximated reference value $\hat{d}(n)$. The adaptive block 34 may be configured as described in relation to FIG. 8.

Figure 3H:
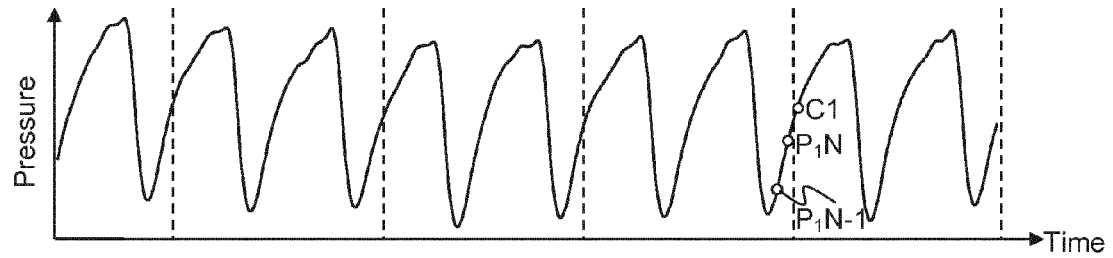

Example III. Reference Value Based on Prediction of Samples Adjacent to the Current Sample FIG. 3H illustrates a third example where the reference value is obtained based on the two preceding data samples $P_1N$ and $P_1N-1$ that are adjacent to the current data sample C1 in the pressure signal. The reference value is calculated by extrapolating the two preceding data samples $P_1N$ and $P_1N-1$. The filter structure 31 in FIG. 9 may be implemented by setting M=2 and $\Delta=1$ (i.e. a delay of one time step) to achieve the data processing in FIG. 3H. Each preceding data sample is multiplied in the multiplication blocks X with a respective weight factor ($W_1$ to $W_m$) and added together in the summation blocks $\Sigma$ to generate an extrapolated or predicted reference value $\hat{d}(n)$. A subtraction algorithm is operated on a current data sample C1, using the predicted reference value $\hat{d}(n)$, to generate an output sample $e(n)$ which is essentially free of a signal component attributable to the first pulse.

Two or more immediately preceding data samples may be used for the prediction or extrapolation. In principle, any previous values may be taken as basis for the prediction or extrapolation of the current data sample, although greater accuracy may be achieved by selecting the preceding data samples closest in time to the current data sample.

The weight factors are suitably set such that the predicted reference value is generated as a function of both the rate of change (derivative) among the preceding data samples and the absolute level among the preceding data samples. For example, reverting to FIG. 3H, the predicted reference value may be given by $\hat{d}(n)=W_1 \cdot P_1N+W_2 \cdot P_1N-1=(W_1+W_2) \cdot P_1N-W_2 \cdot (P_1N-P_1N-1)$, where the first term represents a weighted contribution of the absolute pressure level and the second term represents a weighted contribution of the rate of change in pressure. It is thus apparent that a properly predicted reference value may be generated by a weighted combination of two or more preceding data samples.

The filtering technique according to the third example may be particularly useful when the second pulses are weak relative to the first pulses, e.g. when the magnitude (amplitude) ratio of second pulses to first pulses is less than about 10%, 5% or 1%. With increasing M, the ability of this filtering technique to remove relatively stronger second pulses may be improved.

A variant is obtained by including a block 34 that adaptively determines the weight factors, e.g. as shown and described in relation to FIG. 10.

A general property of including an adaptive filter 36 in the filter structure 31, e.g. as shown in FIGS. 8, 10 and 12, is that the filter structure 31 may be caused, if the preceding data samples comprise both first pulse contributions and second pulse contributions, to converge towards eliminating the first pulse contributions while retaining the second pulse contributions. Thus, the output sample $e(n)$ will contain the second pulse contribution since the filter 36 is unable to reproduce the second pulse contribution in the reference value $\hat{d}(n)$.

Example IV. Recursive Filtering

A fourth example involves a recursive method where the average from previous calculations of the reference values is re-used as a first part together with an additional value as a second part to derive a new average which is then subtracted from a current data sample. This procedure may be repeated for each consecutive time step to isolate the second pulses, if present in the pressure signal. Such a recursive filtering may be implemented by a filter structure 31 as shown in FIG. 7, in which the filter 32 is configured to recursively generate the reference value $\hat{d}(n)$ for each time point n based on a cycle-synchronized data sample $d(n-\Delta)$. As will be shown, the filter 32 may be implemented as a Kalman filter.

Definition of a Kalman Filter

A Kalman filter is in general used to estimate the states in a dynamic system from measurements. Depending on the structure of the dynamic system it may be possible to estimate any number of states from just a single measurement using knowledge about the system structure. As used herein, m designates the number of states. The general structure of a dynamic system (with no control input and one output) in discrete time described in state space form is $$x(n+1)=A(n) \cdot x(n)+v(n)$$

$$d(n)=C(n) \cdot x(n)+e(n) \quad (1)$$

The m states are collected in the vector x, and the measurement d is in our case a scalar, but may in the general case be a vector of any length. The matrix A and vector C determine the structure of the system, and may (as indicated in Eq. 1) be time varying. The disturbances v and e are random vectors of the same dimensions as x and d respectively, and have zero mean values and covariances R and $\sigma^2$, respectively.

The Kalman filter may be configured such that each element in state vector $x(n)$ corresponds to one of the reference values within a current pulse cycle. The Kalman filter is thereby configured to, during each pulse cycle, estimate m reference values collected in the vector $\hat{x}$:

$$\begin{cases} \hat{x}(n+1) = A(n) \cdot \hat{x}(n) + K(n) \cdot [d(n) - \hat{d}(n)] \\ \hat{d}(n) = C(n) \cdot \hat{x}(n) \\ K(n) = \dfrac{A(n) \cdot P(n) \cdot C(n)^T}{\sigma^2 + C(n) \cdot P(n) \cdot C(n)^T} \end{cases} \quad (2)$$

Here, $\hat{d}(n)$ is the estimation made at time n−1 of the first pulse contribution at time n, and $d(n)$ is the current data sample at time n. The expression for $K(n)$ contains a matrix P(n) which is the covariance of the estimation error at time n, i.e. an estimate of the size of the error. It is calculated from:

$$P(n+1) = A(n) \cdot P(n) \cdot A(n)^T - \frac{A(n) \cdot P(n) \cdot C(n)^T \cdot C(n) \cdot P(n) \cdot A(n)^T}{\sigma^2 + C(n) \cdot P(n) \cdot C(n)^T} + R \quad (3)$$

It may be advantageous to identify a structure in which the matrix A and vector C are constant in time, since matrix P and vector K then converge to constant values which may be calculated in advance.

Application of a General Kalman Filter to Estimation of the First Pulse Contribution Each data sample d within the pulse cycle is associated with one state in the model to be estimated. At each point in time, one of these data samples is measured with an error that also includes the effect of the second pulses.

If we assume that the first pulses are constant in time, i.e. the shape being identical from cycle to cycle, then the model of the states is that the states are constant. Hence, matrix A is not only constant, but also identical to the identity matrix, which is a particularly simple matrix that will disappear in all of Equations 1-3 above. With this model one state after the other is measured. Hence, the vector C will not be constant and will change between each measurement. When measuring the first state $x_1$ the vector C will be (1 0 0 0 0 . . . 0), and when the next state $x_2$ is measured it will be (0 1 0 0 . . . 0) and so on.

A Kalman Filter with Constant Parameters

In continuation of the above, it is also possible to find a model where both A and C are constant, which would be advantageous since matrix P and vector K then converge to constant values which may be calculated in advance as indicated above. This is achieved by successively changing the numbering of the states as we change which point is measured. For example, the state that is currently measured may be consistently denoted by $x_1$. For each new data sample, the states are then renumbered. For instance, at the next time interval, the second state is set to the first state, the third state is set to the second state and so on until the last state, which is set to the first state. For m=4 (as an example) this is accomplished by choosing:

$$A = \begin{pmatrix} 0 & 1 & 0 & 0 \\ 0 & 0 & 1 & 0 \\ 0 & 0 & 0 & 1 \\ 1 & 0 & 0 & 0 \end{pmatrix} \quad (4)$$

$$C = (1 \ 0 \ 0 \ 0)$$

With this definition of the C vector, Eq. 2 yields $\hat{d}(n)=\hat{x}_1(n)$, where $\hat{x}_1(n)$ denotes the estimation of the first state. If we assume that the sequence of first pulses are identical, R may be set to zero, i.e. R=0, representing no noise present in the state for the next time interval, i.e. the next state is exactly the same as the previous state was at the last time interval ($x_1(n+1)=x_2(n)$, $x_2(n+1)=x_3(n)$ and so on). Generally however, the measurement noise e is never zero since there will always be some error in the pressure signal and it also contains the varying second pulses.

In practice, it may be assumed that the first pulse profile changes slightly during a measurement session, although involving a very small change between pulse cycles. Hence, R may be set to a very small number. In addition, it can be seen from Eq. 2 and Eq. 3 that it is only the ratio of the covariances R and $\sigma^2$ that matters. The actual value that should be used for this ratio may be determined from practical tests so that the mobility of the profile estimates become reasonable.

With the covariances and the matrix A and vector C determined, the first pulse profile estimates $\hat{x}$ are determined by the initial values for the estimate and for P, and by the measurements (data samples) d. The initial state estimate is normally not known, and the initial value of P may be set to a very large number since it should reflect the uncertainty in the initial estimate. With a very large P, the initial state estimate may be set to zero, since it will immediately be corrected in the next time step. Normally P is thus initially set to a diagonal matrix with large elements, e.g. 1000.

With A and C given by Eq. 4 (for any m), and P started as a diagonal matrix, P will continue to be diagonal matrix throughout the remaining steps. The vector K will then have zeros in all elements except the last one. The matrix P will converge to a constant matrix $\overline{P}$, and the K vector will converge to a constant vector $\overline{K}$. With A and C given by Eq. 4 (for any m), the elements i=1 to m-1 in vector $\overline{K}$ will be zero, and element i=m will be equal to a non-zero value k.

Comparison to a Set of First Order Filters

With the preceding description, all K vector elements except the last one is zero. Hence, all estimates except the last one will be renumbered without any update. Only the next value of the last state will be updated according to the measurement d since state number one will be the last state at the next time interval, when the current state number two will be state number one which will then be updated at the next time interval. Hence, each point in the first pulse will be updated once for each full set of measurements of all states. After the K vector has converged, we get:

$$\hat{x}_i(n+1) = \hat{x}_{i+1}(n) \text{ for all } i=1 \ldots m-1 \quad (5)$$

whereas $$\hat{x}_m(n+1) = \hat{x}_1(n) + k \cdot [d(n) - \hat{d}(n)] \quad (6)$$

Combining Eq. 5 and 6 yields:

$$\hat{x}_m(n+m) = \hat{x}_1(n) + k \cdot [d(n) - \hat{d}(n)] \quad (7)$$

which is equal to $$\hat{d}(n+m) = \hat{d}(n) + k \cdot [d(n) - \hat{d}(n)] \quad (8)$$

This is thus the update we get of the state each time, i.e. every $m^{th}$ measurement, we have a new measurement relating to this point in the pulse cycle. This is the same structure as a normal first order filter, with a time constant of 1/k sample intervals, e.g. corresponding to the time for a full rotor revolution in the case of a peristaltic pump.

From the equations above, it may be shown that K will converge to a value given approximately by $k^2 = m^* R/\sigma^2$, as long as it is far below 1 as it should be. The Kalman filter above may then be replaced with a set of m first order filters with a time constant of 1/k sample intervals.

Figure 14:
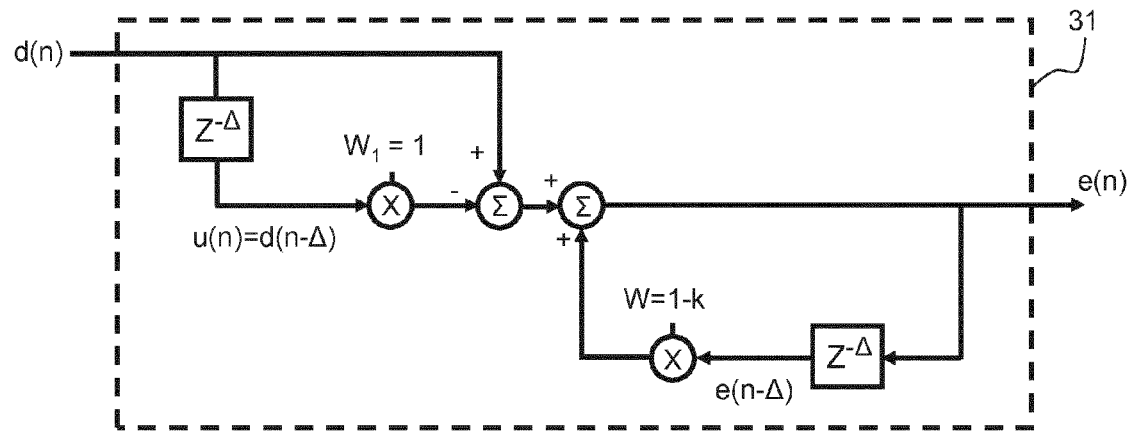

It can be shown that the data processing according to Eq. 8 may be implemented by combining the structures of FIG. 6 and FIG. 13 in series and by using a specific weight factor in the structure of FIG. 13. FIG. 14 illustrates a filter structure 31 that implements the filter structure 31 in FIG. 7 when the filter 32 is a Kalman filter. Specifically, the filter structure 31 in FIG. 14 includes a summation block Σ for calculating a difference value between the current data sample d(n) and a cycle-synchronized data sample u(n), which is obtained by block $Z^{-\Delta}$. A downstream summation block Σ generates the current output sample e(n) as a sum of the difference value and a cycle-synchronized output sample e(n−Δ), which has been generated by block $Z^{-\Delta}$ and then appropriately weighted in by a multiplication block X. The multiplication block X is configured to apply the weight factor W given by 1−k, 0<k<1, such that the filter structure 31 in FIG. 14 implements the above-described Kalman filter.

Elimination of Slow Drifts Using Extra States

In addition to comprising pulses from first and second pulse generators, a component may also be present which is attributable to a slow drift from, e.g., influence from the dialysis fluid side of the dialyzer (cf. 6 in FIG. 4), or movements of blood lines and the pressure sensor. The slow drift may be included in the model by using one or two extra states in the Kalman filter. One extra state may be used to represent the current magnitude of the drift, and the model may then adjust this parameter as a state just as the other states. It is also possible to assume that this extra state moves around slightly by adding white noise (v) in each step. The covariance of this noise may be set much higher than the covariance of the other states, since the first pulse is likely to be more constant than the changing drift. The model for this extra state $x_{m+1}$ would then be:

$$x_{m+1}(n+1)=x_{m+1}(n)+v_{m+1}(n) \quad (9)$$

There is no coupling between this extra state and the other states, and the A matrix is augmented with one extra column and one extra row where all elements are zero except the new diagonal element which is one. The extra state then enters into the measurement equation through an extension of the C vector with an extra 1 at the end $$d(n)=x_1(n)+x_{m+1}(n)+e(n)=C \cdot x(n)+e(n)=(1\ 0\ 0\ 0\ 1)\cdot x(n)+e(n) \quad (10)$$

Optionally, yet another state may be used to estimate the slope of the drift. The model would then assume that the level of the drift is not constant, but is changed by its slope at each new point in time. Instead, the slope would be assumed to be a constant with added noise at each new point in time. With the new state for the slope denoted $x_{m+2}$ and the level still being $x_{m+1}$ we would get the drift model $$x_{m+1}(n+1)=x_{m+1}(n)+x_{m+2}(n)$$

$$x_{m+2}(n+1)=x_{m+2}(n)+v_{m+2}(n) \quad (11)$$

This model is incorporated in the total model by adding two rows and two columns to the original A matrix, where all elements in the first m rows and columns are zero, the two last columns of the penultimate row are both 1, and of the last row 0 and 1 respectively. The covariance value in the matrix R for element m+1 is zero. The measurement equation is only changed by adding one more zero to the C vector since the slope does not enter directly, only through the magnitude.

Elimination of Slow Drifts by Differencing

In the Kalman filter technique described above, the drift in the first pulse profile is estimated as a separate state, which is not coupled to the first pulse. This state cannot be allowed to change too quickly since it incorporates all the measurement noise as well. Additionally, the P matrix will no longer be diagonal, even if the initial value is diagonal, when the extra state is included in the model, rendering the computations more complex and processor demanding.

A different approach utilizes the fact that drift in the first pulse profile may often be deduced from the previous data samples, and assumes that the deviation from the first pulse profile is the same in the next sample. Hence, the deviation from the first pulse profile in one sample may be used to predict the expected deviation in the next sample. This may be achieved by estimating the consecutive differences in the first pulse profile instead of the first pulse profile itself. This may be done using the same equations as above, but with the measurement d(n) now being replaced by the change in pressure value from the previous value to the current one, i.e. d(n)−d(n−1). Thus, step 202 in FIG. 2 may include a sub-step of converting the incoming pressure values by taking the difference between proximate pressure values (e.g. a current pressure value and an immediately preceding pressure value), such that the data samples that are subsequently processed by the Kalman filter (in step 203) are represented as pressure change values instead of pressure values.

In such an implementation, $\hat{d}(n)$ is the estimation of the change in the first pulse contribution at time n. In this approach, the predicted value of the current first pulse contribution will be the sum of the previously measured pressure value and the current estimate of the state $x_1$, instead of only the current estimate of the state $x_1$. To generate the output sample representing the second pulse contribution at time n, $\hat{d}(n)$ may be subtracted from the change in pressure value, d(n)−d(n−1). The estimation of the change is then updated according to Eq. 8 above:

$$\hat{d}(n+m)=\hat{d}(n)+k\cdot[(d(n)-d(n-1))-\hat{d}(n)]. \quad (12)$$

In principle, any previous values may be taken as basis for the prediction or extrapolation of the current data sample, although greater accuracy may be achieved by selecting the preceding data sample closest in time to the current data sample.

Elimination of Slow Drifts by High Pass Filtering

As an alternative to the use of differencing, slow drifts in the first pulse profile may be removed by high pass filtering of $e(n)=d(n)-\hat{d}(n)$ to remove a major part of slow variations. For example, when applied for the purpose of isolating heart pulses in a pressure signal containing signal contributions from a blood pump, a heart and other slower physiological phenomena (such as the effect of breathing), such an embodiment may be optimized to suppress the signal contributions from both the blood pump and the slower physiological phenomena. In this example, the cut off frequency of the high pass filter may have to be well below any low heart rate, e.g. at 0.6 Hz. A further possibility, possibly in combination with the removal of slow disturbances, may be to use a notch filter to eliminate any undesirable residual signal contributions that may remain in the output samples from the Kalman filter.

For the purpose of conceptually explaining embodiments of the present invention, the pressure signal may be said to contain a sequence of "apparent pulses", which are pressure pulses formed by a superposition of first pulses and second pulses when the connection system C is intact, i.e. when a fluid connection is established between the first subsystem S1, e.g. an extracorporeal blood circuit, and the second subsystem S2, e.g. the cardiovascular system of a human subject. The apparent pulses are defined in relation to the above-mentioned pulse cycles, such that each pulse cycle includes one and only one apparent pulse which extends a full pulse cycle. In the examples given herein, it is presumed that the apparent pulses are dominated by the first pulses, such that the first pulses provide a basic shape of the apparent pulses which is modified by the second pulses. However, it is not necessary that the first pulses dominate over the second pulses. When the connection system C is not intact, the apparent pulses are made up of only first pulses (and measurement noise).

Each pressure sensor 4*a*-4*d* in FIG. 1 detects a consecutive time sequence of pressure values. Plotting the sequence of pressure values creates profiles of the pulses, i.e. apparent profiles of the apparent pulses, where the resolution is dependent on the sample rate by which the pressure values are collected.

The apparent profiles may be referred to as a "current apparent profile" and "preceding apparent profiles".

Although embodiments of the invention are generally applicable to other situations, the examples herein are given in relation to first pulses that originate from a (peristaltic) blood pump in an extracorporeal blood treatment system and second pulses that originate from the beating of the heart of a human subject connected to the extracorporeal blood treatment system, e.g. via a vascular access. As used herein, the first pulses may also be denoted "pump pulses" or "pump profiles" (or more generally, "interference pulses" and interference profiles") and the second pulses may also be denoted "heart pulses" and "heart profiles" (or more generally, "physiological pulses" or "physiological profiles").

The embodiment in FIG. 2 may be regarded as a subtraction of preceding apparent pulses from current apparent pulses. The apparent pulses are composed by a number of pressure values or samples. As explained in the foregoing, the subtraction is generally performed sample by sample for each apparent pulse and repeated for each consecutive apparent pulse. For example, the sample by sample calculations may be performed in real-time and on-line during a treatment, although equally applicable off-line, at any part of a pressure signal.

The embodiment in FIG. 2 may thus be seen as a filtering process in which a pump profile is estimated based on one or more preceding apparent pulses and subtracted from the current apparent pulse while leaving the physiological profile in the remaining signal. The level of detail in the resulting physiological profile depends on the number of data samples per cycle, i.e. the number of repetitions of steps 202-204 for each cycle. As used herein, a "profile" is made up of at least three data samples, and preferably at least 5, 10 or 20 data samples, and possibly 100 data samples or more.

Reverting to FIG. 3, it shows a theoretical example of apparent profiles comprising contributions from first and second pulses. In the examples of FIG. 3, the first pulse generator is cyclic with a period of 360 degrees, but with dual members equally distributed, i.e. corresponding to 180 degrees, for instance a dual roller peristaltic pump. Hence, each cycle and thus each complete apparent profile comprises two similar pump profiles, which are illustrated with essentially identical shape for simplicity, and overlaid physiological profiles (heart pulses).

Sampling

Since timing of the pump rotations, both complete rotations and interval between the pump rollers, may not always be constant, the preceding data samples may not always have the same timing within the cycle as the current data sample. In one embodiment, denoted "resembled synchronous sampling" herein, this is remedied by post-processing to adjust the time scale, i.e. by resampling among the data samples, in order to obtain alignment of the current and preceding data samples on the respective cycles. In other words, first data samples that are acquired (sampled) from the pressure signal without (or with insufficient) synchronization with the pump rotation, are subjected to a resampling that generates signal values at a respective given timing (location) within each cycle using interpolation among the first data samples.

The resampling may be facilitated by the use of a timing signal (denoted "tacho-signal" in the following) which is synchronised with the operation of the first pulse generator, e.g. with the angular rotation of the pump rollers of a peristaltic pump. In the tacho-signal, the data samples are associated with a consecutive count which is reset to zero at the same location within each cycle. The total count is the same for each cycle, e.g. in the order of ten thousand counts per cycle. The use of a tacho-signal may improve the time determination of roller revolutions, and thereby also the subtraction process.

In one implementation, the pressure signal is resampled to a rate which is associated with the rotational velocity of the rollers. If the tacho-signal is reset at a same location of the rollers for each cycle, a predefined number of desired sampling points, e.g. 50, may be defined equally distributed between consecutive zero-settings of the tacho-signal, and an interpolation may be performed to find the pressure values (data samples) at these intermediate time points.

When sampling a high frequency signal slowly, the sampling time points will appear to be spread out randomly along the signal, which will result in that the sampled signal will comprise a low frequency instead. This aliasing phenomenon is avoided if the highest frequency in the pressure signal is less than half the sampling frequency, commonly referred to as the Nyquist frequency. Thus, before the sampling, it may generally be preferable to low-pass filter the pressure signal to avoid including frequencies which are higher than half the sampling frequency.

If a tacho-signal is not available, recorded pressure data may instead be analysed for peak detection to determine roller cycle intervals. This may however be obstructed by physical pulses shifting the peaks slightly in time, adding uncertainty to the detection.

In another embodiment, denoted "synchronous sampling" herein, the data samples are sampled synchronously with the motion of the pump revolutions, i.e. at the same respective locations along the circle spanned by the rollers of the pump. The synchronous sampling may be controlled based on the above-mentioned tacho-signal.

Synchronous sampling or resembled synchronous sampling may be of less importance when the sample rate is sufficiently high. For instance, a sample rate of 1000 Hz may be sufficient, i.e. 1000 measurement values or samples registered each second, which represents 1 ms between each sample. For instance, a signal with a sample rate of 1000 Hz which is not resampled to exactly match the exact pump cycles would generate a maximum error, or deviation from the correct value, of only 0.5 ms. Thus, in particular at high sample rates, the inventive technique may be implemented without synchronous sampling or resembled synchronous sampling such that the one or more cycle-synchronized data samples in one or more preceding cycles have a respective location ("best approximation") that may deviate slightly from the exact location of a current data sample in a current pulse cycle. The use of neighbourhood aggregation may further reduce the need for synchronous sampling or resembled synchronous sampling.

Monitoring in an Extracorporeal Blood Flow Circuit

Figure 4:
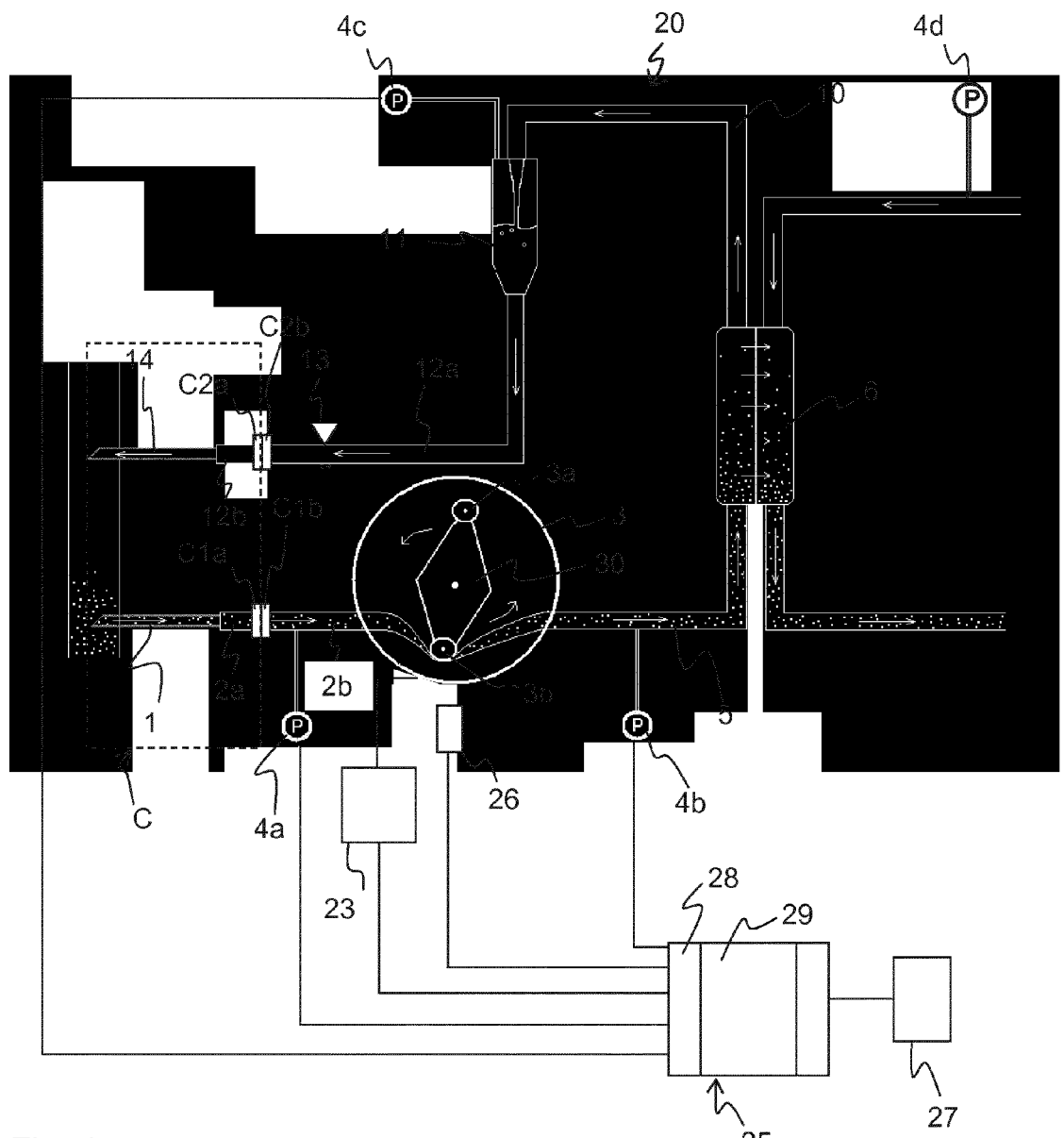
FIG. 4 is a schematic view of a system for hemodialysis treatment including an extracorporeal blood flow circuit.

Below, an extracorporeal blood flow circuit is presented with reference to FIG. 4 as an example of the first sub-system S1 in FIG. 1. In FIG. 4, the extracorporeal blood flow circuit 20 is of the type which is used for dialysis. The extracorporeal blood flow circuit 20 is connected to the cardiovascular system of a human subject (patient) by means of a connection system C. The cardiovascular system corresponds to the second sub-system S2 in FIG. 1. The connection system C comprises an arterial access device 1 for blood extraction (here in the form of an arterial needle), a connection tube segment 2a and a connector C1a. The connection system C also comprises a venous access device 14 for blood reintroduction (here in the form of a venous needle), a connection tube segment 12b, and a connector C2a. The connectors C1a, C2a are arranged to provide a releasable or permanent engagement with a corresponding connector C1b, C2b in the circuit 20 so as to form a blood path between the circuit 20 and the arterial needle 1 and the venous needle 14, respectively. The connectors C1a, C1b, C2a, C2b may be of any known type.

In the illustrated example, the extracorporeal circuit 20 comprises the connector C1b, an arterial tube segment 2b, and a blood pump 3 which may be of peristaltic type, as indicated in FIG. 1. In the illustrated example, the pump 3 comprises a rotor 30 with two rollers 3a, 3b. At the inlet of the pump there is a pressure sensor 4a (hereafter referred to as "arterial sensor") which measures the pressure before the pump in the arterial tube segment 2b. The blood pump 3 forces the blood, via a tube segment 5, to the blood-side of a dialyser 6. Many dialysis machines are additionally provided with a pressure sensor 4b that measures the pressure between the blood pump 3 and the dialyser 6. The blood is led via a tube segment 10 from the blood-side of the dialyser 6 to a venous drip chamber or deaeration chamber 11 and from there back to the connection system C via a venous tube segment 12a and the connector C2b. A pressure sensor 4c (hereafter referred to as "venous sensor") is provided to measure the pressure on the venous side of the dialyser 6. In the illustrated example, the venous sensor 4c measures the pressure in the venous drip chamber 11. Both the arterial needle 1 and the venous needle 14 are connected to the cardiovascular system of a human or animal patient by means of a blood vessel access. The blood vessel access may be of any suitable type, e.g. a fistula, a Scribner-shunt, a graft, etc. Depending on the type of blood vessel access, other types of access devices may be used instead of needles, e.g. catheters. Additionally, a pressure sensor 4d may also be present in a dialysis machine to measure the pressure in a dialysis fluid circuit.

Herein, the "venous side" of the extracorporeal circuit 20 refers to the part of the blood path located downstream of the blood pump 3, whereas the "arterial side" of the extracorporeal circuit 20 refers to the part of the blood path located upstream of the blood pump 3. In the example of FIG. 4, the venous side is made up of tube segment 5, the blood-side of the dialyser 6, tube segment 10, drip chamber 11 and tube segment 12a, and the arterial side is made up of tube segment 2b.

In FIG. 4, a control unit 23 is provided, inter alia, to control the blood flow in the circuit 20 by controlling the revolution speed of the blood pump 3. The extracorporeal blood flow circuit 20 and the control unit 23 may form part of an apparatus for extracorporeal blood treatment, such as a dialysis machine. Although not shown or discussed further it is to be understood that such an apparatus performs many other functions, e.g. controlling the flow of dialysis fluid, controlling the temperature and composition of the dialysis fluid, etc.

Further, in FIG. 4, a surveillance/monitoring device 25 is configured to monitor operation of the circuit 20 and/or the physiological state of the patient, specifically by processing a pressure signal obtained from one or more of the pressure sensors 4a-4d in accordance with the process illustrated in FIG. 2. The processing may involve a process for essentially eliminating or sufficiently suppressing pump pulses originating from the pump 3 in the pressure signal from one of the pressure sensors 4a-4d, while retaining physiological pulses originating from a physiological pulse generator in the patient. Generally, the first pulse generator 3 in FIG. 1 may correspond not only to the pump 3 in FIG. 4, but also to other mechanical pulse generators (not shown) in the circuit 20, such as valves, a pump for dialysis fluid, etc. The physiological pulse generator (corresponding to the second pulse generator 3' in FIG. 1) may be one or a combination of the patient's heart, reflexes, voluntary muscle contractions, non-voluntary muscle contractions, a breathing system, an autonomous system for blood pressure regulation and an autonomous system for body temperature regulation. It is also possible that the physiological pulses originate from a mechanical pulse generator attached to the patient.

A detection of a fault condition may bring the device 25 to activate an alarm and/or stop the blood flow, e.g. by stopping the blood pump 3 and activating one or more clamping devices 13 (only one shown) on the tube segments 2a, 2b, 5, 10, 12a, 12b.

As indicated in FIG. 4, the device 25 may also be connected to the control unit 23. Alternatively or additionally, the device 25 may be connected to a pump sensor 26, such as a rotary encoder (e.g. conductive, optical or magnetic) or the like, that provides the above-mentioned tacho-signal that indicates the frequency and phase of the blood pump 3. In another variant, the pump sensor 26 may be arranged to sense the frequency and phase based on the current or power fed to the motor driving the blood pump 3. The device 25 is tethered or wirelessly connected to a local or remote device 27 for generating an audible/visual/tactile alarm or warning signal. The surveillance device 25 and/or the alarm device 27 may alternatively be incorporated as part of a dialysis apparatus.

In FIG. 4, the surveillance device 25 comprises a data acquisition part 28 for receiving one or more pressure signals from the pressure sensor(s) 4a-4d and, optionally, for pre-processing the incoming pressure signal(s). For example the data acquisition part 28 may include an A/D converter with a required minimum sampling rate and resolution, one or more signal amplifiers, one or more filters to remove undesired signal components in the measurement data, such as offset, high frequency noise and supply voltage disturbances. In this embodiment, data acquisition part 28 acquires the pressure signal as a time sequence of data samples, each representing an instantaneous pressure of the blood in the circuit at the location of the relevant pressure sensor 4a-4d. The data samples are provided as input to a data analysis part 29 that executes the inventive filtering and subsequent monitoring according to the steps in FIG. 2. The steps of filtering and monitoring may be implemented by a combination of a signal processor (25a in FIG. 1) and a memory (25b in FIG. 1).

Embodiments of the invention relate to the monitoring/surveillance carried out by the surveillance device 25, based on the pressure signal. In one example, the monitoring may aim at detecting a disruption of the connection system C between the circuit 20 and the vascular system of the patient, i.e. on either the venous-side or the arterial-side, or both. The disruption may be caused by a dislodgement of the venous or arterial access device 1, 14 from the blood vessel access, i.e. that the access device 1, 14 comes loose from the vascular system of the patient. Alternatively, the disruption may be caused by a disconnection of the venous or arterial access device 1, 14 from the circuit 20, typically by disruption/defective coupling/uncoupling of the connectors C1a, C1b and C2a, C2b, respectively.

With embodiments of the present invention, a functional state or functional parameter of the fluid containing system may be monitored by analysing the filtered signal formed by the above-mentioned sequence of output samples, e.g. by isolating and analysing one or more second pulses in the filtered signal. Valuable information concerning the fluid containing system may also be derived from a detected absence of second pulses.

In extracorporeal blood flow circuits for instance, venous needle dislodgment (VND) may be detected by recognizing that the filtered signal, obtained by processing the pressure signal from the venous pressure sensor 4c, ceases to comprise second (heart and/or breathing) pulses. Various techniques for analysing the filtered signal may be used, for instance by recognizing that the signal magnitude in the filtered signal is below a predetermined threshold, by recognizing that the energy in the filtered signal falls and remains below a threshold for a certain period of time, by identifying a reduced correlation between second pulses in filtered signals obtained from venous and arterial pressure signals indicating loss of the second pulses in the venous pressure signal, by operating statistical techniques on the filtered signal, e.g. to identify a decreased spread of signal values in the filtered signal caused by a lack of second pulses. Additional details of these and other techniques for detecting dislodgment are disclosed in WO97/10013 and WO2009/156174, which are incorporated herein by reference.

To the extent that the pressure signal contains both first and second pulses, the filtered signal will include the second pulses, or part thereof, which may be evaluated for various characteristics for monitoring a functional state or functional parameter of the cardiovascular system of the subject in the case where the second pulses comprise physiological pulses, such as heart pulses, breathing pulses or blood pressure regulating pulses. Such uses of the filtered signal include detecting, presenting, tracking and predicting vital signs, e.g. cardiac or respiratory related such as hypotension prediction, cardiac output and access flow monitoring and blood pressure monitoring, or disordered conditions of the subject such as sneezing, hiccups, vomiting, coughing, blood pressure turbulence, ectopic beats, lack of autonomous regulation, hypotension, disordered breathing, sleep apnea, periodic breathing, hyperventilation, asthmatic attacks, dyspnea, and Cheyne-Stokes respiration. All of these uses or applications may be based on an extraction and analysis of the shape and/or the magnitude and/or the timing of the second pulses in the filtered signal, e.g. as disclosed in WO2010/149726, WO2011/080186, WO2011/080189, WO2011/080190, WO2011/080191 and WO2011/080194, all of which are incorporated herein by reference.

Analysis of the second pulses may also be used to identify a fault condition, e.g. in the connection system C, such as reversed positioning of the access needles 1, 14, where e.g. the shape and/or timing of second pulses may be evaluated for determining the positioning of the needles 1, 14, e.g. as disclosed in WO2011/080188, which is incorporated herein by reference.

The invention has mainly been described above with reference to a few embodiments. However, as readily appreciated by a person skilled in the art, other embodiments than the ones disclosed above are equally possible with the scope and spirit of the invention, which is defined and limited only by the appended patent claims.

For example, the reference value may be calculated as a function of subsequent data samples instead of (or in addition to) preceding data samples, e.g. if a time sequence of data samples is continuously or intermittently buffered in electronic memory (cf. 25b in FIG. 1). For example, the incoming stream of data samples may be entered in a FIFO (First-In, First-Out) buffer in memory (which thus stores a given number of the most recent data samples) and processed to generate a reference value for a current data sample among the data samples in the buffer. The "current" data sample denotes the data sample which is currently being processed to generate a filtered output sample. The skilled person realizes that, using the buffered data samples, the reference value may be calculated as a function of only preceding data samples (i.e. data samples that are measured earlier in time than the current data sample), only subsequent data samples (i.e. data samples that are measured later in time than the current data sample), or both preceding and subsequent data samples. For example, with reference to Example I and Example II above, the cycle-synchronized data sample may be obtained in one or more preceding pulse cycles and/or one or more subsequent pulse cycles. Similarly, with reference to Example III above, the predicted reference value may be generated as a function of two or more immediately subsequent data samples (i.e. by backward projection instead of forward projection), or as a function of data samples on both sides of the current data sample (e.g. by interpolation between one or more preceding data samples and one or more subsequent data samples). The use of subsequent data samples/pulse cycles corresponds to using a positive delay in the filter structures 31 of FIGS. 6-12. The skilled person realizes that the filter structures 31 in FIGS. 6-12 may be modified to use both preceding and subsequent data samples, e.g. by duplicating the respective aggregation block 32 so as to include both blocks $Z^{-\Delta}, \ldots, Z^{-M\Delta}$ and $Z^{\Delta}, \ldots, Z^{M\Delta}$.

Furthermore, the pressure signal may originate from any conceivable type of pressure sensor, e.g. operating by resistive, capacitive, inductive, magnetic or optical sensing, and using one or more diaphragms, bellows, Bourdon tubes, piezo-electrical components, semiconductor components, strain gauges, resonant wires, accelerometers, etc.

Although FIG. 1 indicates that the device 25 is connected to (at least one of) pressure sensors 4a-4d installed in the first sub-system S1, the device 25 may instead be connected to one or more pressure sensors (not shown) installed to measure the fluid pressure in the second sub-system S2. Further, the fluid containing system need not be partitioned into first and second sub-systems S1, S2 connected via a fluid connection C, but could instead be a unitary fluid containing system associated with a first pulse generator and a second pulse generator, and the device 25 may be connected to a pressure sensor installed in the fluid containing system to detect a first pulse originating from the first pulse generator and a second pulse originating from the second pulse generator.

Further, the inventive technique is applicable for monitoring in all types of extracorporeal blood flow circuits in which blood is taken from the systemic blood circuit of the patient to have a process applied to it before it is returned to the patient. Such blood flow circuits include circuits for hemodialysis, hemofiltration, hemodiafiltration, plasmapheresis, apheresis, extracorporeal membrane oxygenation, assisted blood circulation, and extracorporeal liver support/dialysis. The inventive technique is likewise applicable for monitoring in other types of extracorporeal blood flow circuits, such as circuits for blood transfusion, infusion, as well as heart-lung-machines.

The inventive technique is also applicable to fluid systems containing other liquids than blood.

Further, the inventive technique is applicable to remove pressure pulses originating from any type of pumping device, not only rotary peristaltic pumps as disclosed above, but also other types of positive displacement pumps, such as linear peristaltic pumps, diaphragm pumps, as well as centrifugal pumps. In fact, the inventive technique is applicable for removing pressure pulses that originate from any type of periodic pulse generator, be it mechanic or human.

Likewise, the inventive technique is applicable to isolate pressure pulses originating from any type of pulse generator, be it human or mechanic.

The inventive technique need not operate on real-time data, but could be used for processing off-line data, such as a previously recorded measurement signal.

The invention claimed is:

1. A device for processing a time-dependent pressure signal obtained from a pressure sensor in a fluid containing system associated with a first pulse generator and a second pulse generator, wherein the pressure sensor is arranged in the fluid containing system to detect first pulses originating from the first pulse generator and second pulses originating from the second pulse generator, wherein the first pulse generator operates in a sequence of pulse cycles, each pulse cycle resulting in at least one first pulse, said device comprising:
   an input for the pressure signal; and
   a signal processor connected to said input and configured to:
      repetitively obtain a current data sample within a current pulse cycle in the pressure signal;
      calculate, for each current data sample within the current pulse cycle, a reference value as a function of a cycle-synchronized data sample in one or more other pulse cycles in the pressure signal, the cycle-synchronized data sample being obtained to have a location in said one or more other pulse cycles that corresponds to a location of the current data sample in the current pulse cycle; and
      operate a subtraction algorithm on the current data sample, using said reference value obtained for the current data sample as input, so as to generate a current output sample which is essentially free of a signal component attributable to said at least one first pulse.

2. The device of claim 1, wherein the signal processor is configured to calculate the reference value as a function of the cycle-synchronized data sample in an adjacent pulse cycle.

3. The device of claim 2, wherein the signal processor is configured to set the reference value equal to the cycle-synchronized data sample in the adjacent pulse cycle.

4. The device of claim 1, wherein the signal processor is configured to calculate the reference value as an aggregation of the cycle-synchronized data sample and one or more adjacent data samples to the cycle-synchronized data sample in an adjacent pulse cycle.

5. The device of claim 1, wherein the signal processor is configured to calculate the reference value as an aggregation of cycle-synchronized data samples in at least two other pulse cycles.

6. The device of claim 5, wherein the signal processor is configured to calculate the aggregation to include one or more adjacent data samples to each cycle-synchronized data sample in said at least two other pulse cycles.

7. The device of claim 5, wherein the signal processor is configured to calculate the aggregation recursively, by updating a preceding reference value, which corresponds to the reference value and is calculated in a preceding pulse cycle.

8. The device of claim 7, wherein the signal processor is configured to calculate the reference value as a function of the preceding reference value and a difference between the cycle-synchronized data sample in the preceding pulse cycle and the preceding reference value.

9. The device of claim 5, further comprising a Kalman filter, which is configured to receive a time sequence of current data samples obtained within the current pulse cycle as input and estimate a set of states that represent a time sequence of reference values in the current pulse cycle.

10. The device of claim 9, wherein the signal processor is configured to calculate a difference value between the current data sample and the cycle-synchronized data sample, generate a weighted feedback value by applying a weight factor to a cycle-synchronized output sample which is obtained to have a location in one or more preceding pulse cycles that corresponds to a location of the current data sample within the current pulse cycle, and generate the current output sample as a sum of the difference value and the weighted feedback value, wherein the weight factor is selected such that the signal processor implements said Kalman filter.

11. The device of claim 4, wherein the signal processor is configured to calculate the aggregation as a summation of data samples.

12. The device of claim 11, wherein the signal processor is configured to apply a weight factor to each data sample in said summation.

13. The device of claim 12, wherein the signal processor comprises an adaptive filter configured to adaptively determine each weight factor based on a difference between the current data sample and the current output sample.

14. The device of claim 1, wherein the signal processor is configured to obtain the current data sample as a difference between proximate pressure values in the pressure signal.

15. The device of claim 1, wherein the signal processor is configured to obtain first data samples from the pressure signal and obtain each current data sample by interpolation among the first data samples with respect to a respective location within the current pulse cycle.

16. The device of claim 1, wherein the signal processor is configured to obtain the current data sample in synchronization with the pulse cycles.

17. The device of claim 1, further comprising an input for a synchronization signal that represents the pulse cycles of the first pulse generator, wherein the signal processor is responsive to the synchronization signal in at least one of obtaining the current data sample, calculating the reference value, and operating the subtraction algorithm.

18. The device of claim 1, wherein the fluid containing system comprises an extracorporeal blood processing apparatus, a cardiovascular system of a human subject, and a fluid connection between the extracorporeal blood processing apparatus and the cardiovascular system, wherein the first pulse generator is associated with the extracorporeal blood processing apparatus and the second pulse generator is associated with the human subject.

19. The device of claim 1, wherein the signal processor is configured to repetitively obtain the current data sample and calculate the reference value so as to generate a time-sequence of reference values that form an estimated temporal profile of said at least one first pulse within the current pulse cycle.

20. The device of claim 1, wherein the signal processor is configured to operate the subtraction algorithm so as to generate a time-sequence of current output samples which form a temporal profile of the second pulse.

21. The device of claim 1, wherein the signal processor is configured to generate at least three output samples for each current pulse cycle.

22. The device of claim 1, wherein the first pulse generator comprises a peristaltic pump comprising a rotor with at least one roller, and wherein each pulse cycle corresponds to a full rotation of the rotor.

23. The device of claim 1, wherein the first pulse generator comprises a peristaltic pump comprising a rotor with a number rollers, and wherein each full rotation of the rotor generates the same number of pulse cycles as the number of rollers.

24. An apparatus for blood treatment comprising an extracorporeal fluid circuit configured to be connected in fluid communication with a vascular access of a human subject and operable to circulate blood from the cardiovascular system of the human subject through a blood processing device and back to the cardiovascular system, said apparatus further comprising the device as set forth in claim 1.

25. A device for processing a time-dependent pressure signal obtained from a pressure sensor in a fluid containing system associated with a first pulse generator and a second pulse generator, wherein the pressure sensor is arranged in the fluid containing system to detect first pulses originating from the first pulse generator and second pulses originating from the second pulse generator, wherein the first pulse generator operates in a sequence of pulse cycles, each pulse cycle resulting in at least one first pulse, said device comprising:
means for repetitively obtaining a current data sample within a current pulse cycle in the pressure signal;
means for calculating, for each current data sample in the current pulse cycle, a reference value as a function of a cycle-synchronized data sample in one or more other pulse cycles in the pressure signal, the cycle-synchronized data sample being obtained to have a location in said one or more other pulse cycles that corresponds to a location of the current data sample in the current pulse cycle; and
means for operating a subtraction algorithm on the current data sample, using said reference value obtained for the current data sample as input, so as to generate a current output sample which is essentially free of a signal component attributable to said at least one first pulse.

26. A device for processing a time-dependent pressure signal obtained from a pressure sensor in a fluid containing system associated with a first pulse generator and a second pulse generator, wherein the pressure sensor is arranged in the fluid containing system to detect first pulses originating from the first pulse generator and second pulses originating from the second pulse generator, wherein the first pulse generator operates in a sequence of pulse cycles, each pulse cycle resulting in at least one first pulse, said device comprising:
an input for the pressure signal; and
a signal processor connected to said input and configured to:
repetitively obtain a current data sample within the current pulse cycle in the pressure signal;
calculate, for each current data sample within the current pulse cycle, a reference value as an estimate of the current data sample, the estimate being calculated by prediction based on at least two data samples in proximity to the current data sample in the pressure signal; and
operate a subtraction algorithm on the current data sample, using said reference value obtained for the current data sample as input, so as to generate a current output sample which is essentially free of a signal component attributable to said at least one first pulse.

27. The device of claim 26, wherein the signal processor is configured to calculate the prediction by applying a weight factor to each of the at least two data samples.

28. The device of claim 27, wherein the signal processor comprises an adaptive filter configured to adaptively determine each weight factor based on a difference between the current data sample and the current output sample.

29. A device for processing a time-dependent pressure signal obtained from a pressure sensor in a fluid containing system associated with a first pulse generator and a second pulse generator, wherein the pressure sensor is arranged in the fluid containing system to detect first pulses originating from the first pulse generator and second pulses originating from the second pulse generator, wherein the first pulse generator operates in a sequence of pulse cycles, each pulse cycle resulting in at least one first pulse, said device comprising:
means for repetitively obtaining a current data sample within the current pulse cycle in the pressure signal;
means for calculating, for each current data sample within the current pulse cycle, a reference value as an estimate of the current data sample, the estimate being calculated by prediction based on at least two data samples in proximity to the current data sample in the pressure signal; and
means for operating a subtraction algorithm on the current data sample, using said reference value obtained for the current data sample as input, so as to generate a current output sample which is essentially free of a signal component attributable to said at least one first pulse.

30. A method of processing a time-dependent pressure signal obtained from a pressure sensor in a fluid containing system associated with a first pulse generator and a second pulse generator, wherein the pressure sensor is arranged in the fluid containing system to detect first pulses originating from the first pulse generator and second pulses originating from the second pulse generator, wherein the first pulse generator operates in a sequence of pulse cycles, each pulse cycle resulting in at least one first pulse, said method comprising:
repetitively obtaining a current data sample within a current pulse cycle in the pressure signal;
calculating, for each current data sample within the current pulse cycle, a reference value as a function of a cycle-synchronized data sample in one or more other pulse cycles in the pressure signal, the cycle-synchronized data sample being obtained to have a location in said one or more other pulse cycles that corresponds to a location of the current data sample in the current pulse cycle; and
operating a subtraction algorithm on the current data sample, using said reference value obtained for the current data sample as input, so as to generate a current output sample which is essentially free of a signal component attributable to said at least one first pulse.

31. A method of processing a time-dependent pressure signal obtained from a pressure sensor in a fluid containing system associated with a first pulse generator and a second pulse generator, wherein the pressure sensor is arranged in the fluid containing system to detect first pulses originating from the first pulse generator and second pulses originating from the second pulse generator, wherein the first pulse generator operates in a sequence of pulse cycles, each pulse cycle resulting in at least one first pulse, said method comprising:

repetitively obtaining a current data sample within a current pulse cycle in the pressure signal;

calculating, for each current data sample within the current pulse cycle, a reference value as an estimate of the current data sample, the estimate being calculated by prediction based on at least two data samples in proximity to the current data sample in the pressure signal; and operating a subtraction algorithm on the current data sample, using said reference value obtained for the current data sample as input, so as to generate a current output sample which is essentially free of a signal component attributable to said at least one first pulse.

* * * * *